United States Patent [19]
Maris

[11] Patent Number: 6,025,918
[45] Date of Patent: Feb. 15, 2000

[54] APPARATUS AND METHOD FOR MEASUREMENT OF THE MECHANICAL PROPERTIES AND ELECTROMIGRATION OF THIN FILMS

[75] Inventor: Humphrey J. Maris, Barrington, R.I.

[73] Assignee: Brown University Research Foundation, Providence, R.I.

[21] Appl. No.: 09/111,456

[22] Filed: Jul. 7, 1998

[51] Int. Cl.$^7$ .................................................. G01B 11/00
[52] U.S. Cl. .......................... 356/388; 356/389; 356/390; 356/432
[58] Field of Search ................... 356/388, 389, 356/390, 432

[56] References Cited

U.S. PATENT DOCUMENTS

| | | | |
|---|---|---|---|
| 4,484,820 | 11/1984 | Rosencwaig | 374/6 |
| 4,522,510 | 6/1985 | Rosencwaig et al. | 374/7 |
| 4,579,463 | 4/1986 | Rosencwaig et al. | 374/57 |
| 4,632,561 | 12/1986 | Rosencwaig et al. | 356/432 |
| 4,636,088 | 1/1987 | Rosencwaig et al. | 374/5 |
| 4,679,946 | 7/1987 | Rosencwaig et al. | 374/5 |
| 4,710,030 | 12/1987 | Tauc et al. | 356/432 |
| 4,750,822 | 6/1988 | Rosencwaig et al. | 356/445 |
| 4,795,260 | 1/1989 | Schuur et al. | 356/400 |
| 4,854,710 | 8/1989 | Opsal et al. | 356/432 |
| 4,952,063 | 8/1990 | Opsal et al. | 356/432 |
| 4,999,014 | 3/1991 | Gold et al. | 356/382 |
| 5,042,951 | 8/1991 | Gold et al. | 356/369 |
| 5,042,952 | 8/1991 | Opsal et al. | 356/432 |
| 5,074,669 | 12/1991 | Opsal | 356/445 |
| 5,546,811 | 8/1996 | Rogers et al. | 73/800 |

OTHER PUBLICATIONS

W. Lee Smith et al. "Ion implant monitoring with thermal wave technology". Appl. Phys.Lett.. vol. 47.No. 6, Sep. 15, 1985. p. 584–586.

J. Opsal et al. "Thermal and plasma wave depth profiling in silicon". Appl. Phys. Lett. vol. 47 No. 5, Sep. 1, 1985. p. 498–500.

A. Rosencwaig et al. "Thin–film thickness measurements with thermal waves". Appl. Phys. Lett., vol. 43 No. 2, Jul. 15, 1983. p. 166–168.

A. Rosencwaig et al. "Detection of thermal waves through optical reflectance". Appl. Phys. Lett., vol. 46 No. 11, Jun. 1, 1985. p. 1013–1015.

A. Elci et al. "Physics of Ultrafast Phenomena in Solid State Plasmas". Solid–State Electronics, vol. 21, 1978, p. 151–158.

D.H. Auston et al. "Picosecond Spectroscopy of Semiconductors". Solid–State Electrtonics, vol. 21, 1978, p. 147–150.

D.H. Auston et al. "Picosecond Ellipsometry of Transient Electron–Hole Plasmas in Germanium". Physical Review Letters, vol. 32 No. 20. May 20, 1974 p. 1120–1123.

R.J. Stoner et al. "Kapitza conductance and heat flow between solids at tempertures from 50 to 300K". Physical Review B, vol. 48, No. 22, Dec. 1, 1973 p. 16 373– 16 387.

(List continued on next page.)

*Primary Examiner*—Frank G. Font
*Assistant Examiner*—Reginald A. Ratliff
*Attorney, Agent, or Firm*—Ohlandt, Greeley, Ruggiero & Perle

[57] ABSTRACT

A method for characterizing a sample comprising the steps of depositing the sample on a substrate, measuring a first change in optical response of the sample, changing the lateral strain of the sample, measuring a second change in optical response of the sample, comparing the second change in optical response of with the first change in optical response and associating a difference between the second change and the first change in optical response with a property of interest in the sample. The measurement of the first change in optical response is made with the sample having an initial lateral strain. The measurement of the second change in optical response is made after the lateral strain in the sample is changed from the initial lateral strain to a different lateral strain. The second change in optical response is compared to the first change in optical response to find the difference between the second change and the first change.

27 Claims, 14 Drawing Sheets

OTHER PUBLICATIONS

R.J. Stoner et al. "Measurements of the Kapitza Conductance between Diamond and Several Metals". Physical Review Letters, vol. 68 No. 10, Mar. 9, 1992 p. 1563–1566.

S. Sumie et al. "A New Method of Photothermal Displacement Measurement by Laser Interferometric Probe". Jpn. J. Appl. Phys. vol. 31 Pt. 1, No. 11, 1992 p. 3575–3583.

S. Sumie et al. J.Appl. Phys. 76(10), Nov. 15, 1994 p. 5681–5689.

F.E. Doany et al. "Carrier lifetime versus ion–implantation dose in silicon on sapphire". Appl. Phys. Lett. 50(8), Feb. 23, 1987 p. 460–462.

D.A. Young et al. "Heat Flow in Glasses in a Picosecond Timescale". Dept. of Engineering, Brown University, Providence, RI. 1986. p. 49–51.

"Surface Generation and Detection of Phonons By Picosecond Light Pulses" C. Thomsen et al. Physical Review B. vol. 34, No. 6, Sep. 15, 1986, The American Physical Society, p. 4129–4138.

"Sound Velocity and Index of Refraction of AlAs Measured By Pico–second Ultrasonics" , H.T. Grahn, et al. Appl. Phys. Lett. 53(21), Nov. 21, 1988 pp. 2023–2024.

"Elastic Properties of Silicon Oxynitride Films Determined by Pico–second Acoustics" by H.T. Grahn et al., Appl. Phys. Lett. 53 (23), Dec. 5, 1988, pp. 2281–2283.

"Noninvasive picosecond ultrasonic detection of ultrathin interfacial layers: CFx at the Al/Si interface" by G. Tas, R. J. Stoner and H.J. Maris, Appl Phys. Lett. 61 (15). Oct. 12, 1992 pp. 1787–1789.

"Detection Of Thin Interfacial Layers By Picosecond Ultrasonics" by G. Tas, R.J. Stoner J. Maris, G.W. Rubloff, G.S. Oehrlein and J.M. Halbout, Mat. Res. Soc. Symp. Proc. vol. 259 1992 Materials Research Society, pp. 231 236.

"Studies of High–Frequency Acoustic Phonons Using Picosecond Optical Techniques", H.J. Maris, et al., Phonon Scattering in Condensed Matter 5, Eds. A.C. Anderson, J.C. Wolfe, Springer, Berlin, 1986, p. 374.

"Picosecond Photoinduced Electronic And Acoustic Effects In a–Si:H Based Multilayer Structures", H.T. Grahn, et al., Journal of Non–Crystalline Solids 97&98 (1987) p. 855–858.

"Picosecond Acoustics As A Non–Destructive Tool For The Characterization Of Very Thin Films", C. Thomsen, et al., Thin Solid Films, 154 (1987) p. 217–223.

"Time–resolved study of vibrations of a–Ge:H/a–Si:H multilayers", H.T. Grahn,et al Physical Review B, vol. 38, No. 9, Sep. 15, 1988.

"Picosecond Ultrasonics", Holger T. Grahn, et al., IEEE Journal of Quantum Electronics, vol. 25, No. 12, Dec. 1989.

Nondestructive Testing of Microstructures by Picosecond Ultrasonics, H.N. Lin, et al., Journal of Nondestructive Evaluation, vol. 9, No. 4, 1990.

"Phonon Attenuation and Velocity Measurements in Transparent Materials by Picosecond Acoustic Interferometry", H.N. Lin, et al. Journal of Applied Physics, vol. 69, p. 3860 (Apr. 1991).

Attenuation of longitudinal–acoustic phonons in amorphous $SiO_2$ at frequencies up to 440 $GH_z$, T.C. Zhu, et al. . The American Physical Society 1991.

"Detection of Titanium Silicide Formation And Phase Transformation by Picosecond Ultrasonics", H.N. Lin, et al., Mat. Res. Soc. Proc. Advanced Metalization and Processing for Semiconductor Devices III, vol. 260, p. 221 (1992).

"Ultrasonic Experiments At Ultra–High Frequency With Picosecond Time–Resolution", H.N. Lin, et al., IEEE Ultrasonics Symp.90.

"Picosecond Optics Studies Of Vibrational And Mechanical Properties of Nanostructures", H.J. Maris, et al., AMD–vol. 140, Acousto–Optics and Acoustic Microscopy ASME 1992.

"Picosecond optical studies of amorphous diamond and diamondlike carbon: Thermal conductivity and longitudinal sound velocity", Christopher J. Morath, et al, J. Appl. Phys., vol. 76, No. 5, Sep. 1, 1994, p. 2636.

"Study of vibrational modes of gold nanostructures by picosecond ultrasonics", H.N. Lin, et al., J. Appl. Phys. vol. 73, No. 1, Jan. 1, 1993.

"Nondestructive detection of titanium disilicide phase transofrmation by picosecond ultrasonics", H.N. Lin, et al., Applied Physics Letters, No. 61, p. 2700, 1992.

O.B. Wright et al. "Laser Picosecond Acoustics in Various Types of Thin Film", Japanese Journal of Applied Physics, vol. 31, (1992).

G.J. Flechtner et al., "Measurements of Atomic Sodium in Flames by Asynchronous Optical Sampling: theory and experiment", Applied Optics, vol. 31, No. 15, May 20, 1992.

O.B. Wright, "Thickness and sound velocity measurement in thin transparent films with laser picosecond acoustics", Journal of Applied Physics, vol. 71, #4, Feb. 15, 1992.

O.B. Wright, et al. "High Resolution Laser Picosecond Acoustics in Thin Films" Symp. on Physical Acoustics, Belgium, 1990.

C.A. Paddock et al., "Transient Thermoreflectance From Thin Metal Films", J. Appl. Phys. 60, Jul. 1, 1986.

D.M. Pennington et al., "Direct Measurement of the Thermal Expansion of a Surface Using Transient Gratings", Optical Society.

K.A. Svinarich et al., "Picosecond Acoustic Pulse REflection From A Metal–Metal Interface", Dept. of Physics, Wayne State University.

G.L. Eesley et al., Generation and Detection of Picosecond Acoustic Pulses in Thin Metal Films, Appl. Phys. Lett. 50, Mar. 23, 1987.

B.M. Clemens et al., "Relationship between interfacial strain and the elastic response of multilayer metal films", Physical Review Letter, vol. 61, No. 20, Nov. 14, 1988.

G. Tas et al., "Picosecond Ultrasonic Investigation of Thin Interfacial Layers Between Films and a Substrate", IBM T.J. Watson Research Center.

P.A. Elzinga et al., "Pump/probe method for fast analysis of visible spectral signatures utilizing asynchronous optical sampling", Appl. Optics vol. 26, No. 19 Nov. 1, 1987.

R.J. Kneisler et al., "Asynchronous optical sampling: a new combustion diagnostic for potential use in turbulent, high––pressure flames", 1989 Optics Letters, vol. 14. No. 5.

BEFORE APPLICATION OF STRAIN

AFTER APPLICATION OF STRAIN

APPARATUS AND METHOD FOR MEASUREMENT OF THE MECHANICAL PROPERTIES AND ELECTROMIGRATION OF THIN FILMS

CROSS-REFERENCE TO A RELATED PATENT APPLICATION

This patent application is related to U.S. patent application Ser. No. 08/924,792 filed Feb. 25, 1998, entitled "Ultrafast Optical Technique for the Characterization of Altered Materials", which is continuation in part of U.S. patent application Ser. No. 08/519,666 filed Aug. 25, 1985 now U.S. Pat. No. 5,706,094 dated Jan. 6, 1998. +gi

STATEMENT OF GOVERNMENT RIGHTS

This invention was made with Government support under Contract No. DE-FG02-86ER45267 awarded by the Department of Energy. The Government has certain rights in this invention.

FIELD OF THE INVENTION

This invention relates generally to a method for characterizing a sample composed of one or more thin films through the use of electromagnetic radiation to generate and detect stress pulses. From measurements of the propagation characteristics of the stress pulses in the sample the mechanical properties of the sample are determined.

BACKGROUND OF THE INVENTION

Currently, in the semiconductor industry there is a great interest in the characterization of thin films. Integrated circuits are made up a large number of thin films deposited onto a semiconductor substrate, such as silicon. The thin films include metals to make connections between the transistors making up the chip, and insulating films to provide insulation between the metal layers (see: S. A. Campbell, The Science and Engineering of Microelectronic Fabrication, Oxford University Press, (1996)). The metal films (interconnects) are typically arranged as a series of patterned layers. At the present time there may be 4 or 5 layers of interconnects. It is likely that as more complex integrated circuits are developed which will require a greater number of interconnections the number of layers will increase. Metals of current interest include, for example, aluminum, copper, titanium and silicides. Insulating films include, for example, oxide glasses of various compositions and polymers.

When a stress is applied to a material there is a change in shape of the material which can be described by means of the strain tensor. Different materials, and even the same material at different temperatures, or prepared by a different method, exhibit a different response to an applied stress (see: F. A. McClintock and A. Argon, Mechanical Behavior of Materials, Addison-Wesley, (1965)).

For an elastic material when the stress is removed the material returns to its original size and shape. For such materials there is a range of stress over which the strain is, to a good approximation, linearly proportional to the applied stress. Within this range of stress such materials are said to be linearly elastic. In the regime of linear elasticity the material is characterized by a number of parameters called elastic constants. These parameters are coefficients which relate the elements of the stress tensor to elements of the strain tensor. The elastic constants are dependent on the composition of the material. They may also be affected to some extent by the microstructure of the material. This microstructure, in turn, is influenced by the manner in which the material is prepared. The microstructure includes the crystalline phase, the size and orientation of crystalline grains, the presence and arrangement of dislocations and point defects within the material.

All materials show substantial deviations from elastic behavior when the stress exceeds some value. Such materials are referred to as anelastic. For these materials, the material does not return to its original size or shape after application of a stress. The strain that results from the application for a period of time $\tau_{stress}$ of a stress of a given magnitude $\sigma$ depends in a complicated way on the value of $\tau_{stress}$ and $\sigma$. For some materials there is no permanent change in shape or size unless a exceeds a critical value $\sigma_{yield}$; this stress is referred to as the yield stress for the onset of plastic flow. For other materials the application of even a small stress results in a small strain which increases steadily with the time $\tau_{stress}$. For anelastic materials the response of the material to an applied stress will, in general, be substantially affected by the history of the sample. For example, a sample may show a different response to an applied stress of given magnitude according to the number of times that the stress has been applied. For an anelastic material the complete characterization of the mechanical properties is much more complicated than for an elastic material. The anelastic properties are affected considerably by the microstructure of the material. The anelastic behavior of a film may also be significantly influenced by the thickness and other dimensions of the film and possibly also by the properties of the films adjacent to it, or by the substrate if the film is directly deposited onto the substrate. Generally, it is more likely that anelasticity will be important the higher the temperature of the sample.

Stress in thin films making up an integrated circuit can arise from a number of mechanisms. These include the following.

(A) The film may be deposited at an elevated temperature onto the substrate, or on top of another film deposited previously. When the resulting structure is cooled the difference between the thermal expansion coefficient of the substrate and the deposited film will result in the film being under stress.

(B) The film may be deposited by a process that results in a built-in stress, even if the film is grown at ambient temperature. For example, if a crystalline film is grown epitaxially on a substrate there will generally be a stress that arises from the difference in the unstrained lattice parameters of the two materials.

(C) After a film is grown it may be subject to further processing which changes the stress in the film. For example, ion irradiation or plasma bombardment can cause the stress in a film to be modified.

(D) When an electrical current flows through a metal film a different type of stress can result (see: C. Bosvieux and J. Friedel, Journal of Physics and Chemistry of Solids, Volume 23,123,(1962); see also: H. B. Huntington and A. R. Grone, Journal of Physics and Chemistry of Solids, Volume 20,76, (1961)) The interaction between the current and the atoms in the film can result in a force on the atoms. This force can be considered to be a form of stress at the microscopic level. This stress can result in a permanent displacement of the atoms from their original positions referred to as electromigration. This displacement of the atoms can result in a change in the external shape and dimensions of the film. This change in shape and dimensions can be considered to amount to a special type of plastic strain.

It is desirable to have available a method to characterize the mechanical properties of thin films.

This invention is concerned with the response of thin films to an applied stress, including stresses that result in plastic flow of the film. Previously, the following methods have been used for characterization of the mechanical properties of thin films. In a first method, the film may be deposited onto a substrate having a thermal expansion coefficient different than the thermal expansion coefficient of the thin film. The temperature of the substrate is then raised. Because of the difference between the thermal expansion coefficient of the film and the expansion coefficient of the substrate, the film is strained with respect to its stress-free state at the same temperature. The stress in the film can be determined by measuring the curvature that is induced in the wafer. (See: M. F. Doerner, D. S. Gardner and W. D. Nix, Journal of Materials Research, Volume 1, 845–851, (1986), (hereafter Doerner et al.) and C. A. Volkert, C. F. Alofs and J. R. Liefting, Journal of Material Research, Volume 9, 1147–1155 (1994)). The curvature is commonly measured either via a differential capacitance technique or by laser deflection. Consider a film which lies in the xy-plane and whose surface is normal to the z-direction. The radius of curvature R of the wafer is measured together with the thickness d of the film and the thickness $d_s$ of the substrate. The non-zero components of the stress tensor of the film are then $\sigma_{zz}=0$, $\sigma_{xx}=\sigma_{yy}=-P$, where P is found from the relation $$P=(Y_s d_s^2)/[6R(1-v_s)d] \qquad (1)$$

where $Y_s$ is Young's modulus for the substrate and $v_s$ is Poisson's ratio for the substrate. If the substrate takes on a shape which is convex on the side where the film is deposited this indicates that the stress is compressive, (i.e. P is positive and the stress is negative).

In this measurement the temperature can be changed continuously, or in discrete steps, so as to change the strain. The radius of curvature R is measured continuously and the stress calculated. Thus the stress-strain relation can be determined. This method has two disadvantages: (i) the relationship between stress and strain at a fixed definite temperature cannot be determined because in order to produce the strain it is necessary to vary the temperature; (ii) the measurement of wafer curvature can only be used to give the average stress over a large area of the film. It cannot be used to measure stress within a small region of a film, or to find the stress in a film deposited onto a small area of the substrate.

A second method of the prior art, uses a nanoindenter to perform hardness measurements. A very small indenter tip is pressed into the film. (See: Doerner et al.) The force applied to the tip and the tip displacement are measured. This method has the disadvantage that the stress and the strain have a complicated spatial variation in the vicinity of the tip, i.e. they are not uniform throughout the film. This complicates the analysis and interpretation of the measurements.

A third method of the prior art, uses electron microscopy to measure the changes in the film geometry that result from applied stress. When the stress applied to a film exceeds the yield stress and plastic flow occurs, the surface of a film often becomes uneven and this can be detected by electron microscope observations. Similarly, electromigration often results in the appearance of characteristic features, such as hillocks, on the surface of films. (See: I. A. Blech and E. S. Meieran, Journal of Applied Physics, Volume 40, 485–491 (1969)). Scanning electron microscopy has the disadvantage that significant time is required to make a measurement. A second difficulty is that conventional scanning electron microscopes often cannot accommodate the large diameter wafers (200 or 300 mm) that are involved in modern chip fabrication. It is also possible to use transmission electron microscopy to measure changes in microstructure that result from plastic deformation and electromigration. However, this measurement requires either that the film be removed from the substrate or that special samples be prepared in which the substrate underneath some part of the length of a metal film is etched away.

In a fourth method of the prior art, the film or films of interest are completely or partially removed from the substrate. Mechanical contact is made to the film in some way and stress is then directly applied. The resulting strain is then measured. This method has the disadvantage that since the film is removed from the substrate the sample is destroyed.

OBJECTS OF THE INVENTION

It is a first object of the invention to provide an improved method for the determination of the elastic and anelastic response of thin films to applied stresses through the use of an optical method employing a short optical pulse to generate a mechanical strain pulse and a second optical pulse to detect the propagation of the strain pulse. The propagating mechanical strain pulse probes the mechanical properties of the sample.

It is a further object of the invention to detect changes in the geometry of metal films that result from electromigration.

It is a further object of this invention to perform such measurements non-destructively and with micron or submicron lateral resolution within the sample.

SUMMARY OF THE INVENTION

In accordance with a first method of the present invention a method for characterizing a sample is provided. The method comprises the steps of depositing the sample on a substrate, measuring a first change in optical response of the sample, changing a lateral strain of the sample, measuring a second change in optical response of the sample, comparing the second change with the first change and associating a difference between the second change and first change with a property of interest in the sample. The sample has an initial lateral strain when the first change in optical response is measured. The lateral strain in the sample is changed from the initial lateral strain to a different lateral strain and the second change in optical response is measured after the sample has the different lateral strain.

In accordance with a second method of the present invention, a method for measuring a rate of electromigration in a thin metal film is provided. The method comprises the steps of measuring a first change in optical response of the metal film, passing an electric current through the metal film, measuring a second change in optical response of the metal film, comparing the second change to the first change to find a difference therebetween and relating the difference to the rate of electromigration in the metal film.

In accordance with a first embodiment of the present invention, a non-destructive system for characterizing a thin film is provided. The non-destructive system comprises a stage, means for applying an optical pump pulse and an optical probe pulse to the film, means for detecting a change in optical response with respect to time and means for changing strain in the thin film. The stage holds a substrate of a predetermined thickness. The film is located on a first side of the substrate. The means for applying the pump pulse and the probe pulse apply the pump pulse and probe pulse to a free surface of the thin film. The probe pulse is temporally delayed from the pump pulse. The means for detecting a change in optical response detect the change in optical response with respect to time of the probe pulse reflected from the surface of the thin film. The means for changing the strain in the thin film change the strain from an initial strain value to a different strain value.

In accordance with a third method of the present invention, a method for measuring a rate of electromigration in a sample is provided. The method comprises the steps of measuring a first transient optical response of the sample, heating a portion of the sample, measuring a second transient optical response of the sample and relating a difference between the second transient optical response and the first transient optical response to the rate of electromigration in the sample. Heating a portion of the sample induces a temperature gradient in the sample. The second transient optical response of the sample is measured from the heated portion of the sample.

BRIEF DESCRIPTION OF THE DRAWINGS

The above set forth and other features of the invention are made more apparent in the ensuing Detailed Description of the Invention when read in conjunction with the attached Drawings, wherein:

FIG. 1A' illustrates a portion of FIG. 1A in greater detail;

DETAILED DESCRIPTION OF THE INVENTION

The teaching of this invention is practiced with an optical generator and a detector of a stress wave within a sample. The sample is comprised of a substrate having at least one metal film deposited thereon. The metal film may be made of copper or aluminum or any other suitable metal. The thickness of the film could range from 100 Å to 10$\mu$. In this system, a non-destructive first light pulse is directed onto the sample. This first light pulse, referred to hereafter as a pump beam, is absorbed in a thin layer at the top surface of the sample. When the pump beam is absorbed, the temperature of the surface layer is increased, and the layer tries to expand. This launches a strain pulse which propagates into the film. When the strain pulse reaches the film-substrate interface, a part of the strain pulse is reflected back towards the top surface of the film. When the strain pulse reaches the top surface of the film, the change in strain associated with the propagating pulse results in a change in the optical constants of the metal. This change leads to a sudden change in the optical response of the metal film, such as a change $\Delta R(t)$ in the optical reflectivity R of the top surface of the metal film. This change or transient of the optical response is measured by means of a second light pulse directed at the sample. This second light pulse, referred to hereafter as a probe beam, is time-delayed relative to the pump beam. Physical properties of the film are measured by observing the transient optical response (e.g. changes in the reflected probe beam intensity) and comparing the difference in the time dependence of the transients whilst manipulating the metal films in some way.

Figure 1A:
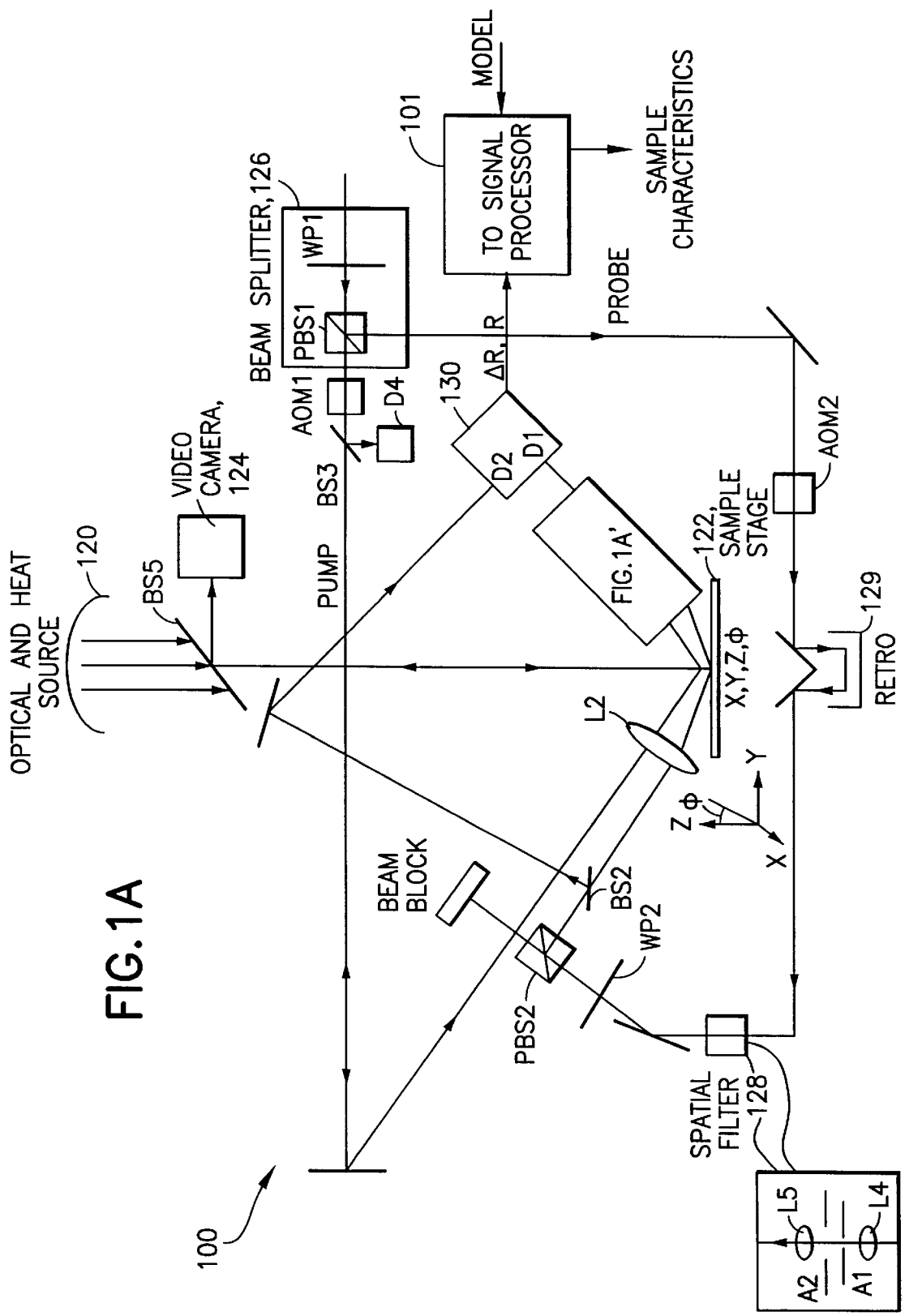
FIG. 1A is a block diagram of a first, embodiment of an ultra-fast optical system that is suitable for use in practicing this invention, specifically, a parallel, oblique beam embodiment.

Reference is now made to FIG. 1A and FIG. 1A', collectively referred to below as FIG. 1A, for illustrating a first embodiment of an apparatus 100 suitable for practicing this invention. This embodiment is referred to as a parallel, oblique embodiment.

This embodiment includes an optical/heat source 120, which functions as a variable high density illuminator, and which provides illumination for a video camera 124 and a sample heat source for temperature-dependent measurements under computer control. An alternative heating method employs a resistive heater embedded in a sample stage 122. One advantage of the optical heater is that it makes possible rapid sequential measurements at different temperatures, or at one stabilized temperature.

The video camera 124 provides a displayed image for an operator, and facilitates the set-up of the measurement system. Appropriate pattern recognition software can also be used for this purpose, thereby minimizing or eliminating operator involvement. BS5 is a broad band beam splitter that directs video and a small amount of laser light to the video camera 124. The camera 124 and processor 101 can be used to automatically position the pump and probe beams on a measurement site.

The sample stage 122 (see also FIG.4) is preferably a multiple-degree of freedom stage that is adjustable in height (global z-axis), position (global x and y-axes), and optionally tilt ($\phi$), and allows motor controlled positioning of a portion of the sample relative to the pump and probe beams. The global z-axis is used to translate the sample vertically into the focus region of the pump and probe, the global x and y-axes translate the sample parallel to the focal plane, and the tilt axes adjust the orientation of the stage 122 to establish a desired angle of incidence for the probe beam. This is achieved via position sensitive detector PSD1 and a signal processor 101, as described below.

In an alternative embodiment, the optical head may be moved relative to a stationary, tiltable stage 122' (not shown). This is particularly important for scanning large objects (such as 300 mm diameter wafers, or mechanical structures, etc.) In this embodiment the pump beam, probe beam, and video signal can be delivered to or from the translatable head via optical fibers or fiber bundles.

The pump-probe beam splitter 126 splits an incident laser beam pulse (preferably of picosecond or shorter duration) into pump and probe beams, and includes a rotatable half-wave plate (WP1) that rotates the polarization of the unsplit beam. WP1 is used in combination with polarizing beam splitter PBS1 to effect a continuously variable split between pump and probe power. This split may be controlled by the computer by means of a motor to achieve an optimal signal to noise ratio for a particular sample. The appropriate split depends on factors such as the reflectivity and roughness of the sample. Adjustment is effected by having a motorized mount rotate WP1 under computer control.

A first acousto-optic modulator (AOM1) chops the pump beam at a frequency of about 1 MHz. A second acousto-optic modulator (AOM2) chops the probe beam at a frequency that differs by a small amount from that of the pump modulator AOM1. The use of AOM2 is optional in the system illustrated in FIG. 1A. Optionally, the AOMs may be synchronized to a common clock source, and may further be synchronized to the pulse repetition rate (PRR) of the laser that generates the pump and probe beams. Optionally an electro-optic modulator can be used in place of acousto-optic modulators AOM1 or AOM2.

A spatial filter 128 is used to preserve at its output a substantially invariant probe beam profile, diameter, and propagation direction for an input probe beam which may vary due to the action of the mechanical delay line shown as a retroreflector 129. The spatial filter 128 includes a pair of apertures A1 and A2, and a pair of lenses L4 and L5. An alternative embodiment of the spatial filter incorporates an optical fiber, as described above. If the profile of the probe beam coming from the mechanical delay line does not vary appreciably as the retroreflector 129 is moved, the spatial filter 128 can be omitted.

WP2 is a second adjustable halfwave plate which functions in a similar manner with PBS2 to the WP1/PBS1 combination of the beam splitter 126. The part of the beam passing through the beam splitter PBS1 impinges on a beam block. Beam splitter BS2 is used to direct a small fraction of the probe beam onto reference detector D2. The output of D2 is amplified and sent through a low pass filter to give an electrical signal LF2 which is proportional to the average intensity of the incident probe beam.

The probe beam after passing through BS2 is focused onto the sample by lens L2. After reflection from the sample the beam is collimated and after passing polarizer 132 is incident on photodetector D1. From the output of D1 two electrical signals are derived. The first signal LF1 is obtained by passing the amplified output of D1 through a low pass filter to give an electrical signal proportional to the average intensity of the incident probe beam. The second signal HF1 is obtained by passing the amplified output of D1 through a high pass filter which passes the frequency of modulation used for AOM1.

The low frequency signals LF1 and LF2 can be used to determine the reflectivity of the sample, after allowance is made for fixed losses in both optical paths. The signal LF2 and the average (dc) output of detector D4 give a measure of the intensity of the pump and probe beams. These signals are fed to a computer, for example the signal processor 101, which in turn controls motorized waveplates WP1 and WP2. The computer is programmed to adjust these waveplates so as to give the desired total optical power and pump/probe ratio for a sample exhibiting a particular reflectivity.

The linear polarizer 132 is employed to block scattered pump light polarization, and to pass the probe beam. The beamsplitter BS1 is used to direct a small part of the pump beam, and optionally a small part of the probe beam, onto a first Position Sensitive Detector (PSD1) that is used for autofocusing, in conjunction with the processor 101 and movements of the sample stage 122. The PSD1 is employed in combination with the processor 101 and the computer-controlled stage 122 (tilt and z-axis) to automatically focus the pump and probe beams onto the sample to achieve a desired focusing condition.

The detector D1 may be used in common for reflectometry, ellipsometry, and transient optical embodiments of this invention. However, the resultant signal processing is different for each application. For transient optical measurements, the DC component of the signal is suppressed, such as by subtracting reference beam input D2, or part of it as needed, to cancel the unmodulated part of D1, or by electrically filtering the output of D1 so as to suppress frequencies other than that of the modulation. The small modulated part of the signal is then amplified and stored. For ellipsometry, there is no small modulated part, rather the entire signal is sampled many times during each rotation of the rotating compensator (see discussion of FIG. 1B below), and the resulting waveform is analyzed to yield the ellipsometric parameters. For reflectometry, the change in the intensity of the entire unmodulated probe beam due to the sample is determined by using the D1 and D2 output signals (D2 measures a signal proportional to the intensity of the incident probe). Similarly, additional reflectometry data can be obtained from the pump beam using detectors D3 and D4. The analysis of the reflectometry data from either or both beams may be used to characterize the sample. The use of two beams is useful for improving resolution, and for resolving any ambiguities in the solution of the relevant equations.

A third beamsplitter BS3 is used to direct a small fraction of the pump beam onto detector D4, which measures a signal proportional to the incident pump intensity. A fourth beamsplitter BS4 is positioned so as to direct a small fraction of the pump beam onto detector D3, which measures a signal proportional to the reflected pump intensity.

Figure 1B:
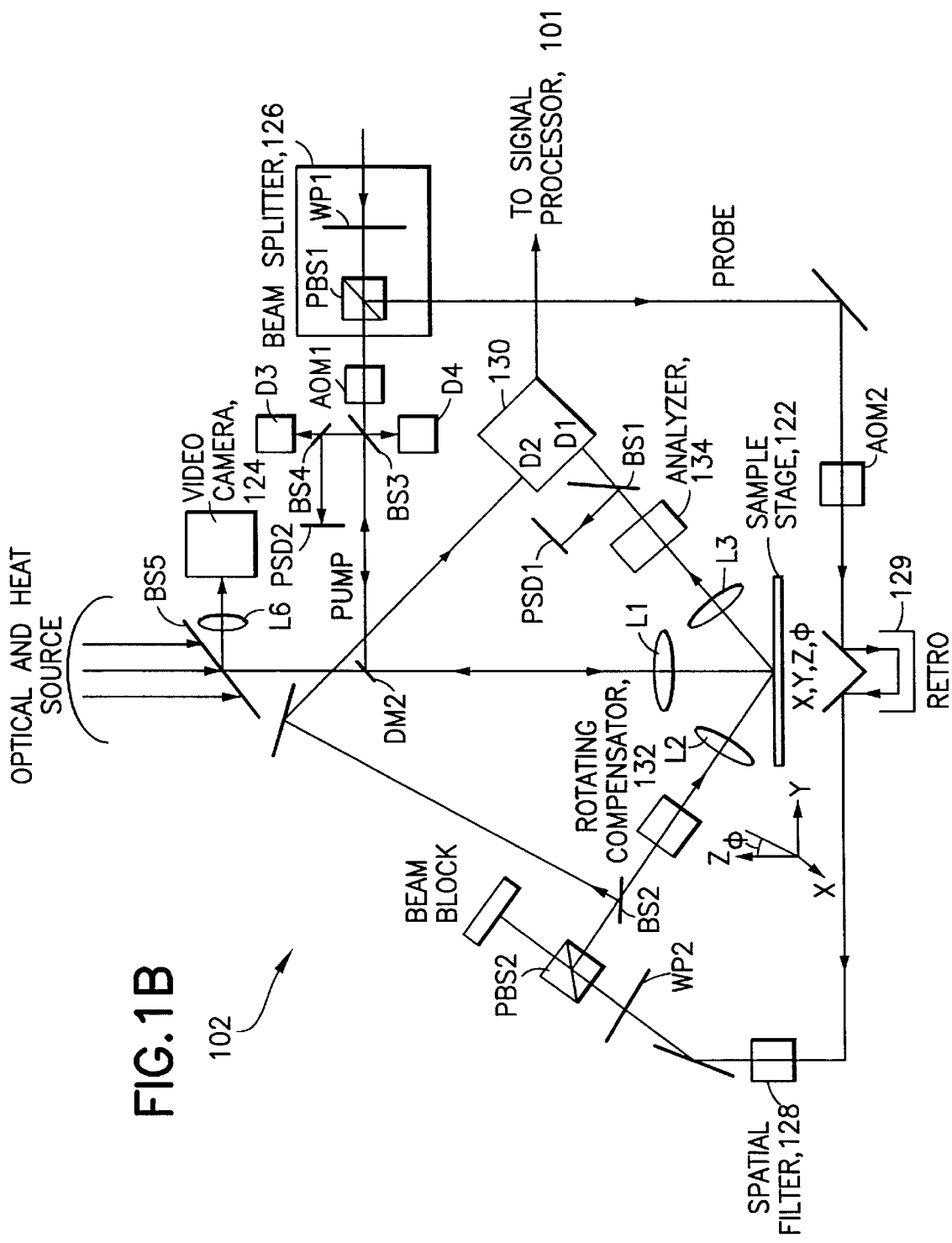
FIG. 1B is a block diagram of a second embodiment of an ultra-fast optical system that is suitable for use in practicing this invention, specifically, a normal pump, oblique probe embodiment.

FIG. 1B illustrates a normal pump beam, oblique probe beam embodiment of apparatus 102. Components labelled as in FIG. 1A function in a similar manner, unless indicated differently below. In FIG. 1B there is provided the above-mentioned rotating compensator 132, embodied as a linear quarter wave plate on a motorized rotational mount, and which forms a portion of an ellipsometer mode of the system. The plate is rotated in the probe beam at a rate of, by example, a few tens of Hz to continuously vary the optical phase of the probe beam incident on the sample. The reflected light passes through an analyzer 134 and the intensity is measured and transferred to the processor 101 many times during each rotation. The signals are analyzed according to known types of ellipsometry methods to determine the characteristics of the sample (transparent or semitransparent films). This allows the (pulsed) probe beam to be used to carry out ellipsometry measurements.

The ellipsometry measurements are carried out using a pulsed laser, which is disadvantageous under normal conditions, since the bandwidth of the pulsed laser is much greater than that of a CW laser of a type normally employed for ellipsometry measurements.

The ellipsometry measurement capability is useful in performing certain of the embodiments of the method described below, wherein it is required to determine the index of refraction of a film layer disposed over a substrate. Also, the ellipsometry measurement capability is useful wherein it may be advantageous to be able to determine the index of refraction of one or more film layers in a sample composed of several films.

If transient optical measurements are being made, the rotating compensator 132 is oriented such that the probe beam is linearly polarized orthogonal to the pump beam. The analyzer 134 may be embodied as a fixed polarizer, and also forms a portion of the ellipsometer mode of the system. When the system is used for transient optical measurements the polarizer 134 is oriented to block the pump.

The analyzer 134 may be embodied as a fixed polarizer, and also forms a portion of the ellipsometer mode of the system. When used in the ellipsometer mode, the polarizer 134 is oriented so as to block light polarized at 45 degrees relative to the plane of the incident and reflected probe beam.

The embodiment of FIG. 1B further includes a dichroic mirror (DM2), which is highly reflective for light in a narrow band near the pump wavelength, and is substantially transparent for other wavelengths.

It should be noted in FIG. 1B that BS4 is moved to sample the pump beam in conjunction with BS3, and to direct a portion of the pump to D3 and to a second PSD (PSD2). PSD2 (pump PSD) is employed in combination with the processor 101, computer controlled stage 122 (tilt and z-axis), and PSD1 (Probe PSD) to automatically focus the pump and probe beams onto the sample to achieve a desired focusing condition. Also, a lens L1 is employed as a pump, video, and optical heating focussing objective, while an optional lens L6 is used to focus the sampled light from BS5 onto the video camera 124.

Figure 1C:
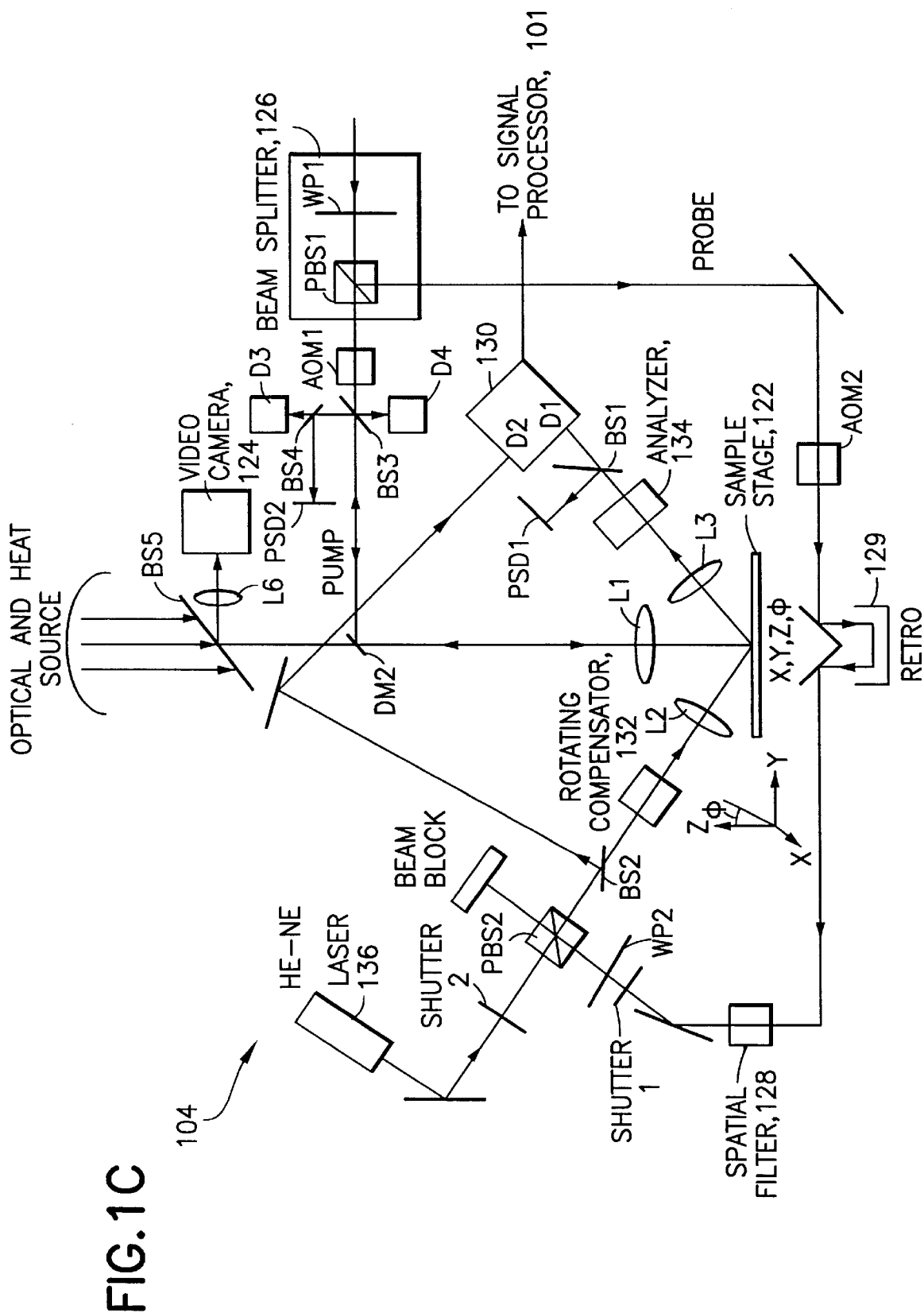
FIG. 1C is a block diagram of a third embodiment of an ultra-fast optical system that is suitable for use in practicing this invention, specifically, a single wavelength, normal pump, oblique probe, combined ellipsometer embodiment.

Reference is now made to FIG. 1C for illustrating an embodiment of apparatus 104, specifically a single wavelength, normal pump, oblique probe, combined ellipsometer embodiment. As before, only those elements not described previously will be described below.

Shutter 1 and shutter 2 are computer controlled shutters, and allow the system to use a He—Ne laser 136 in the ellipsometer mode, instead of the pulsed probe beam. For transient optical measurements shutter 1 is open and shutter 2 is closed. For ellipsometer measurements shutter 1 is closed and shutter 2 is opened. The HeNe laser 136 is a low power CW laser, and has been found to yield superior ellipsometer performance for some films.

Figure 1D:
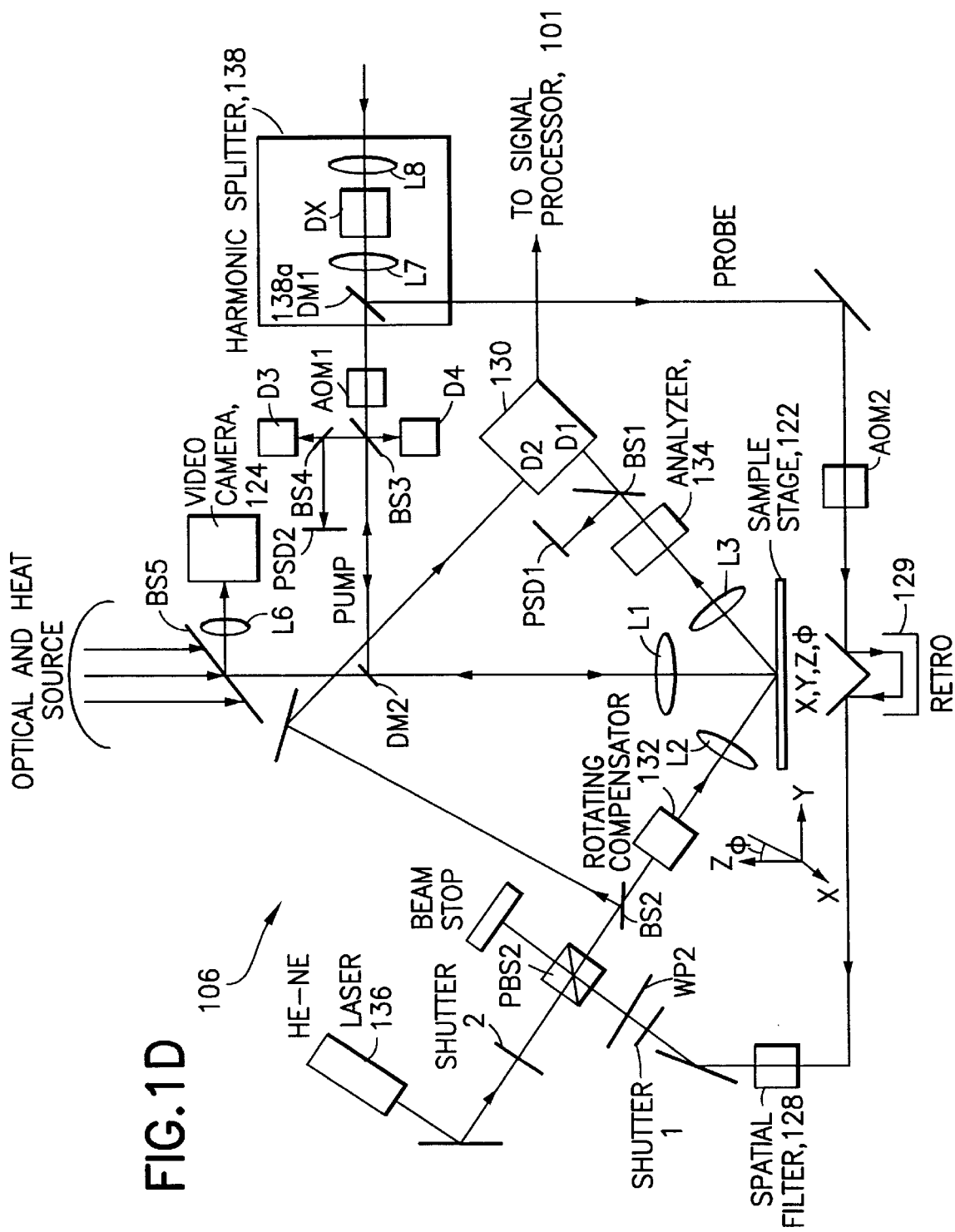
FIG. 1D is a block diagram of a fourth embodiment of an ultra-fast optical system that is suitable for use in practicing this invention, specifically, a dual wavelength, normal pump, oblique probe, combined ellipsometer embodiment.

FIG. 1D is a dual wavelength embodiment 106 of the system illustrated in FIG. 1C. In this embodiment the beamsplitter 126 is replaced by a harmonic splitter, an optical harmonic generator that generates one or more optical harmonics of the incident unsplit incident laser beam. This is accomplished by means of lenses L7, L8 and a nonlinear optical material (DX) that is suitable for generating the second harmonic from the incident laser beam. The pump beam is shown transmitted by the dichroic mirror (DM1 138a) to the AOM1, while the probe beam is reflected to the retroreflector. The reverse situation is also possible. The shorter wavelength may be transmitted, and the longer wavelength may be reflected, or vice versa. In the simplest case the pump beam is the second harmonic of the probe beam (i.e., the pump beam has one half the wavelength of the probe beam).

It should be noted that in this embodiment the AOM2 can be eliminated and instead a color filter F1 can be used in front of the detector D1 in order to reduce the amount of light reaching the detector D1. F1 is a filter having high transmission for the probe beam and the He—Ne wavelengths, but very low transmission for the pump wavelength.

Figure 1E:
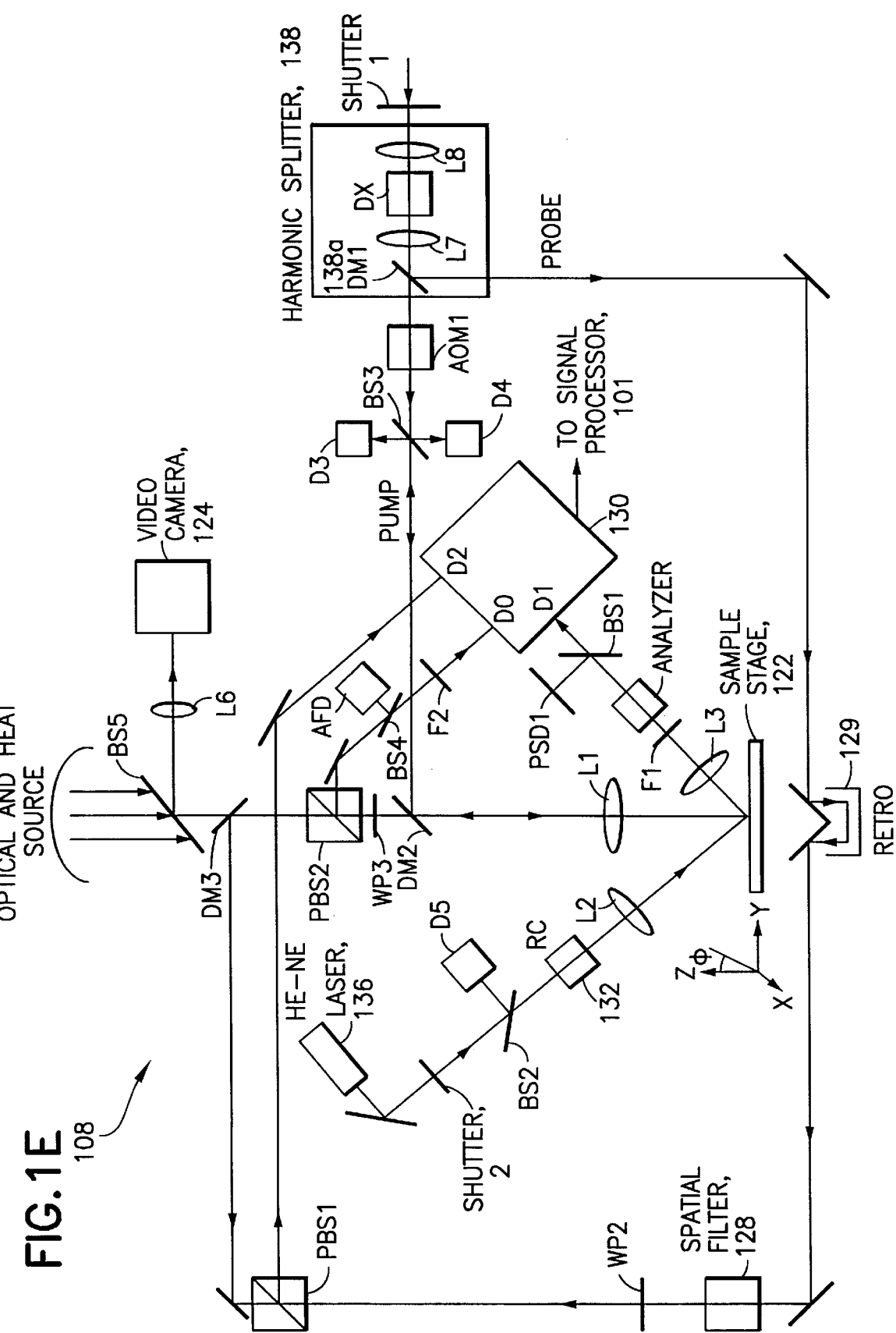
FIG. 1E is a block diagram of a fifth embodiment of an ultra-fast optical system that is suitable for use in practicing this invention, specifically, a dual wavelength, normal incidence pump and probe, combined ellipsometer embodiment.

Finally, FIG. 1E illustrates a normal incidence, dual wavelength, combined ellipsometer embodiment 108. In FIG. 1E the probe beam impinges on PBS2 and is polarized along the direction which is passed by the PBS2. After the probe beam passes through WP3, a quarter wave plate, and reflects from the sample, it returns to PBS2 polarized along the direction which is highly reflected, and is then directed to a detector D0 in detector block 130. D0 measures the reflected probe beam intensity.

In greater detail, WP3 causes the incoming plane polarized probe beam to become circularly polarized. The handedness of the polarization is reversed on reflection from the sample, and on emerging from WP3 after reflection, the probe beam is linearly polarized orthogonal to its original polarization. BS4 reflects a small fraction of the reflected probe onto an Autofocus Detector AFD.

DM3, a dichroic mirror, combines the probe beam onto a common axis with the illuminator and the pump beam. DM3 is highly reflective for the probe wavelength, and is substantially transparent at most other wavelengths.

D1, a reflected He—Ne laser 136 detector, is used only for ellipsometric measurements.

It should be noted that, when contrasting FIG. 1E to FIGS. 1C and 1D, that the shutter 1 is relocated so as to intercept the incident laser beam prior to the harmonic splitter 138.

Figure 9:
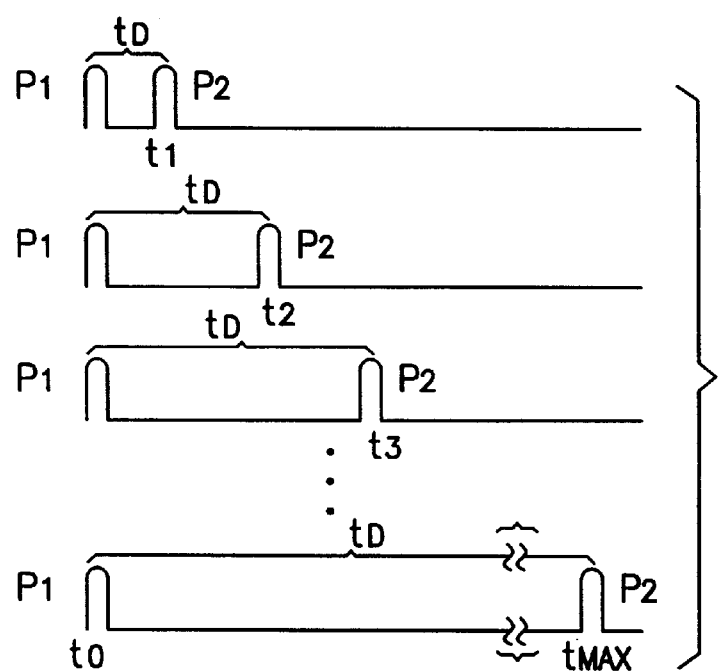
FIG. 9 illustrates a timed sequence of a plurality of consecutive pump pulses and corresponding probe pulses.

Based on the foregoing descriptions, a selected one of these presently preferred embodiments of measurement apparatus provide for the characterization of samples in which a short optical pulse (the pump beam) is directed to an area of the surface of the sample, and then a second light pulse (the probe beam) is directed to the same or an adjacent area at a later time. The retroreflector 129 shown in all of the illustrated embodiments of FIGS. 1A–1E can be employed to provide a desired temporal separation of the pump and probe beams. FIG. 9 illustrates various time delays ($t_D$)

between the application of a pump beam pulse (P1) and a subsequent application of a probe beam pulse (P2), for times ranging from $t_1$ to $t_{MAX}$.

Figure 1F:
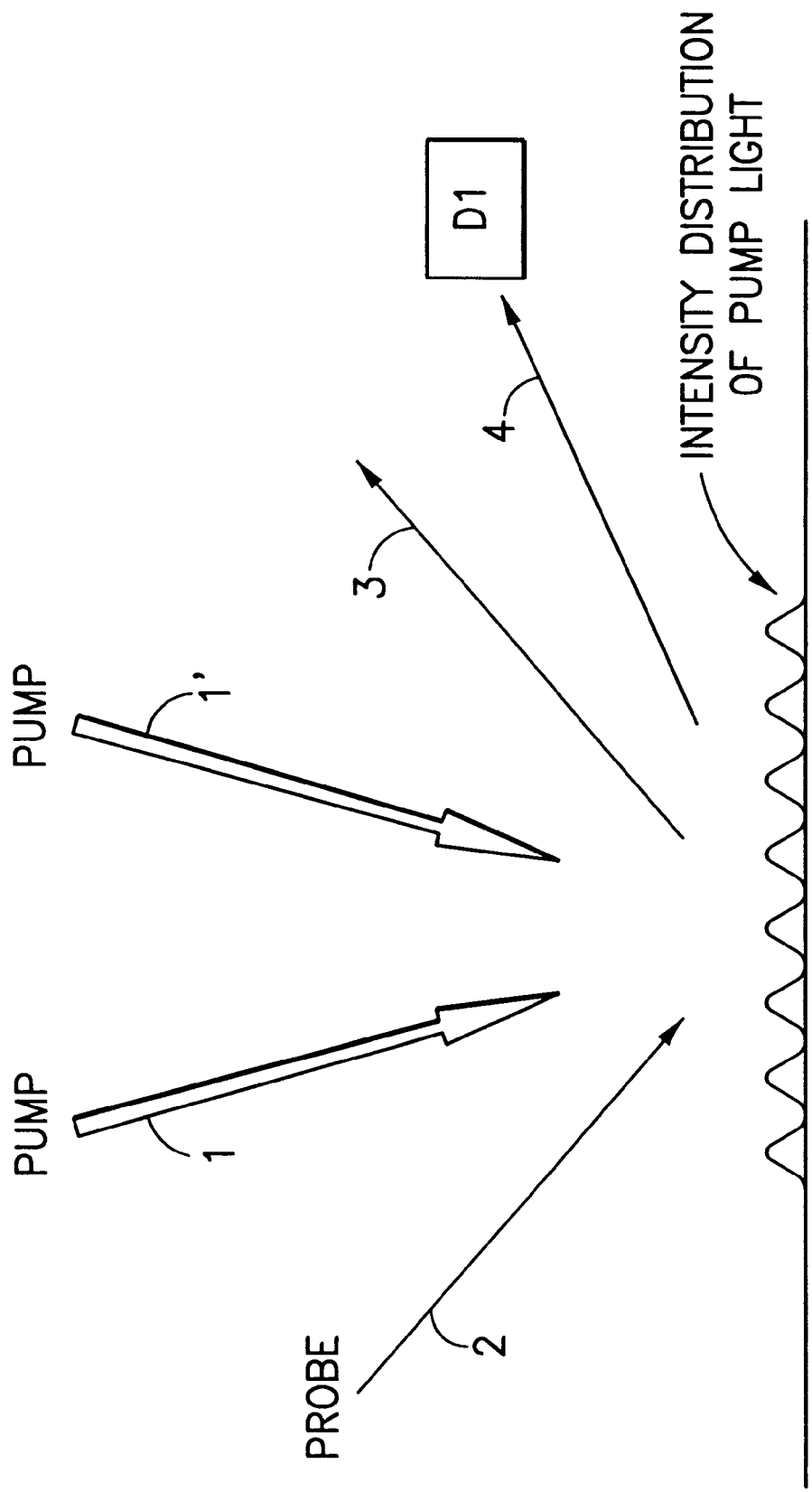
FIG. 1F illustrates the operation of a transient grating embodiment of this invention, wherein the pump pulse is divided and made to interfere constructively and destructively at the surface of the sample.
Figure 1A:
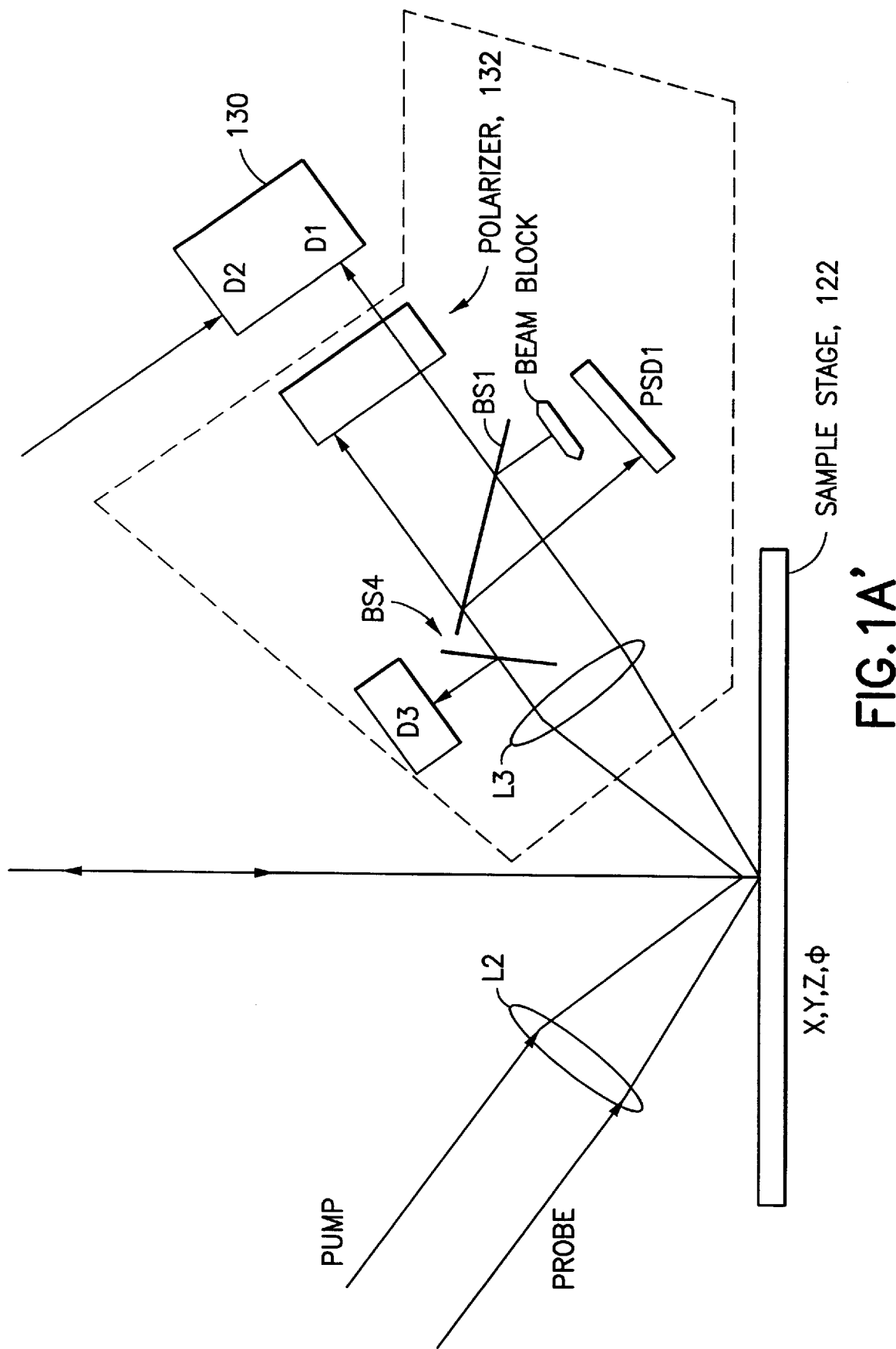

The five embodiments 100, 102, 104, 106 and 108, as described above, have in common the feature that a sequence of pump pulses are generated and directed at the surface of the sample. Each pump pulse illuminates the same area of the sample with an intensity that varies smoothly across the area. It is also within the scope of this invention to make measurements of the transient optical response by means of the induced transient grating method. (See: D. W. Phillion, D. J. Kuizenga, and A. E. Siegman, Appl. Phys. Lett. 27, 85 (1975)). To induce a transient grating each pump pulse is divided into two or more components by means of a beam splitter or beam splitters, these components then pass through separate optical paths, and are then all directed onto the same area of the surface of the sample. If the different components are directed onto the surface with different angles there will be places within the area where the different components interfere constructively and places where the interference is destructive. Thus the total intensity of the pump light will vary across the sample surface. In the case that only two components 1 and 1' are present, as shown in FIG. 1F, the intensity will vary periodically across the sample surface. The periodicity of the intensity, i.e. the spacing between successive points of maximum intensity, is determined by the wavelength of the pump light and the angles at which the different components of the pump light are incident onto the surface. Then the amount of light absorbed in the structure will vary periodically across the surface, and the propagating strain pulse generated by the pump light will vary periodically across the sample. Consequently, the transient changes in the optical properties of the sample which result from the return of the strain pulse to the top surface will also vary periodically across the surface of the sample. This variation of the transient changes in the optical properties of the sample is equivalent to the production of a transient diffraction grating coinciding with the sample surface. When probe light 2 is incident on the area excited by the pump, a part 4 of the probe light will be diffracted, i.e. a part of the probe light will be reflected in a direction, or directions, away from the direction 3 of specular reflection. Measurement of the intensity of this diffracted probe light by means of the detector Di as a function of the time delay t between the application of the pump and probe beams provides an alternate method for the characterization of the transient optical response produced in the sample.

Figure 2:
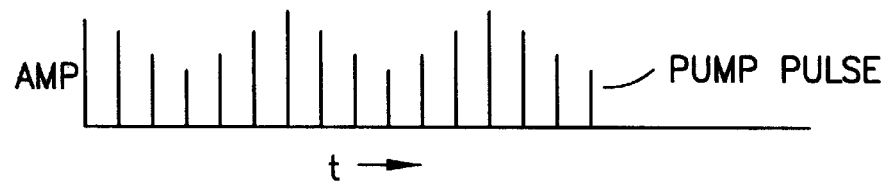
FIG. 2 illustrates a pulse train of pump beam pulses having an overlying low frequency intensity modulation impressed thereon.

Typical characteristics of the light pulses employed in the systems 100–108 of FIGS. 1A–1E are as follows. The pump pulse has an energy of approximately 0.001 to 100 Nj per pulse, a duration of approximately 0.01 psecs to 100 psec per pulse, and a wavelength in the range 200 nm to 4000 nm. The pulse repetition rate (PRR) is in the range of 100 Hz to 5 Ghz and, as is shown in FIG. 2, the pump pulse train may be intensity modulated at a rate of 1 Hz to 100 Mhz, depending on the PRR. The pump pulse is focussed to form a spot on the sample surface of diameter in the range of approximately 10 micrometers to 20 micrometers, although smaller spot sizes, and hence smaller lateral resolutions, can also be employed.

Figure 3A:
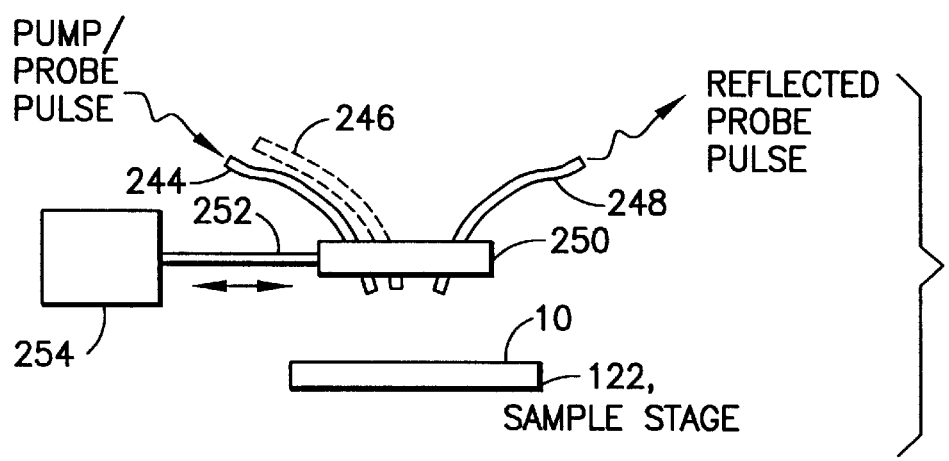
FIG. 3A illustrates a further embodiment wherein one or more optical fibers are positioned for delivering the pump beam and/or probe beam and for conveying away the reflected probe beam.

Referring to FIG. 3A, it is also within the scope of the teaching of this invention to deliver the pump pulse, or the probe pulse, or both the pump and probe pulses, through an optical fiber 244. Alternatively, a second input fiber 246 can be provided, whereby the pump pulse is delivered through the fiber 244 and the probe pulse is delivered through the fiber 246. Another fiber 248 can also be employed for receiving the reflected probe pulse and delivering same to the photodetector (not shown). For this embodiment the end of the optical fiber(s) are affixed to and supported by a holding stage 250. The holding stage 250 is preferably coupled through a member 252 to an actuator 254, such as a linear actuator or a two degree of freedom positioning mechanism. In this manner the reliability and repeatability of the measurement cycle is improved, in that the size and position of the focussed pump, probe, or pump and probe beams on the sample surface are independent of minor changes in the direction or profile of the laser output beams, or changes in the profile of the probe beam associated with the motion of any mechanical stage that may be used to effect the delay $t_D$. Preferably, the angular orientation between the end of the probe beam delivery fiber and the end of the reflected probe beam fiber is such as to optimize the gathering of reflected probe beam light from the sample surface. It is also within the scope of this invention to use one or more lenses following the fiber or fibers, in order to focus the output beams from the fibers onto the sample surface, or to collect the reflected probe light and to direct it into the fiber 248 of FIG. 3A.

Figure 3B:
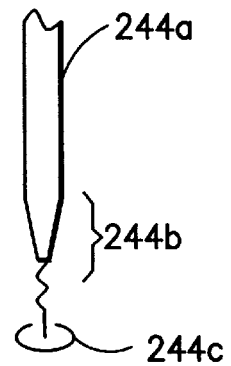
FIG. 3B illustrates a terminal end of a fiber optic that has been reduced in cross-sectional area for delivering an optical pulse to a small surface area of a sample.

FIG. 3B shows an embodiment wherein a terminal portion 244b of a pump and/or probe beam delivery fiber 244a is reduced in diameter, such as by stretching the fiber, so as to provide a focussed spot 244c having a diameter that is less than the normal range of optical focussing. When coupled with the embodiment of FIG. 3A this enables the pump and or probe optical pulse to be repeatably delivered to a very small region of the sample surface (e.g., to a spot having a diameter ≦ one micrometer), regardless of any changes that are occurring in the optical path length of the probe beam.

The apparatus 100, 102, 104, 106 and 108, as described above, are capable of measuring the transient change in the reflectivity ΔR(t) of the probe beam. By detecting the transient change in reflectivity ΔR(t) of the probe beam, the time interval τ corresponding to the round trip time of the stress pulse in the sample may be determined. The time interval τ for the round trip time of the stress pulse in the sample is, $$\tau = 2\frac{d}{v} \tag{2}$$

where d is the film thickness and v is the sound velocity. The time interval τ for the round trip time of the stress pulse in the sample is also coincident to the time between the application of the pump beam pulse and detection, by the apparatus 100, 102, 104, 106 and 108, of the change in optical reflectivity ΔR of the reflected probe pulse arising from the returning strain pulse. Thus, a determination of the time interval τ when there is an echo feature in ΔR(t) of the reflected probe beam (see FIGS. 6A–6B) caused by the returning stress pulse can be used to find the round trip time of the stress pulse in the sample film. Alternatively, in the transient diffraction grating mode of the apparatus 100, 102, 104, 106 and 108 the detection of the diffracted probe beam is coincident with the return of the periodically varying strain pulse to the surface of the thin film (see FIG. 1F). Thus, in the case of the diffraction grating mode, determination of the time interval τ when the returning strain pulse diffracts the probe beam can be used to find the round trip time of the stress pulse in the film. The time interval τ is identified and recorded by the processor 101 of the apparatus 100, 102, 104, 106 and 108.

Figure 4:
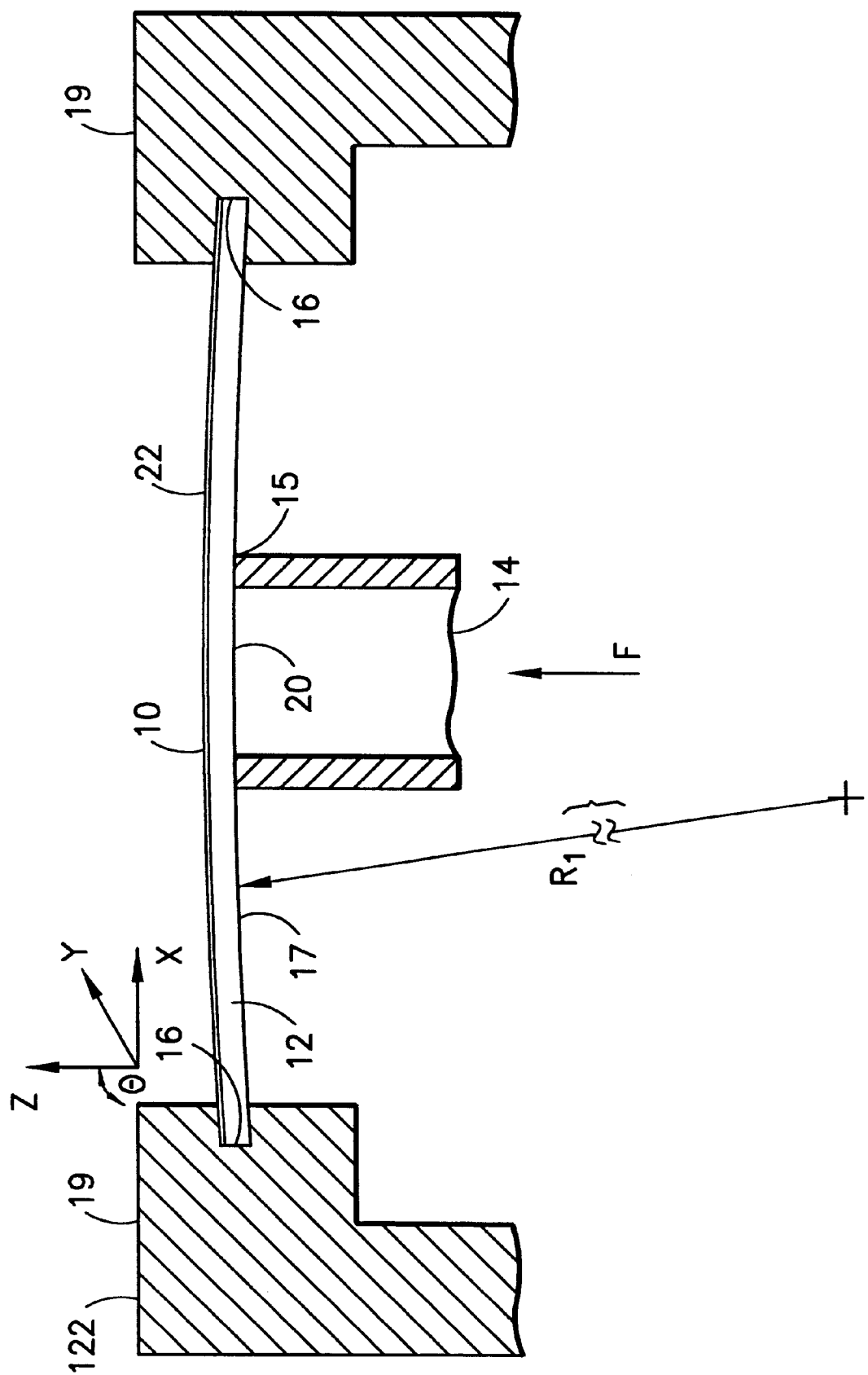
FIG. 4 is a schematic cross-sectional view of a sample to be characterized in accordance with a first method of the invention, wherein the sample is deposited on a substrate which is clamped at its boundaries and has a force applied thereto.

Referring now to FIG. 4, there is shown a schematic cross-sectional view of the sample thin film 10 deposited on a substrate 12. The substrate 12 is held on the sample stage 122 of the apparatus 100, 102, 104, 106 and 108 described above. In a preferred embodiment of the invention, the substrate 12 onto which the metal film 10 is deposited is a silicon wafer. In alternate embodiments of the invention, the substrate may be of any other suitable type of material. The substrate or wafer 12 has a generally circular perimeter 16 (not shown). Silicon wafers that are currently used in chip fabrication have a thickness that is usually between 100 and 1000 μm. The wafer 12 is mounted so that its perimeter 16 is clamped in a clamp 19. Force is applied perpendicular to the plane of the wafer 12 by pressing the end 15 of a hollow cylinder 14 against the back surface 17 of the wafer 12 (see FIG. 4). In this way, the wafer 12 becomes curved over its entire surface thereby forming a general hemihead shape. At each point the curvature of the wafer 12 can by specified in terms of the radii of curvature $R_1$ and $R_2$ (not shown) along two principal orthogonal directions. These radii of curvatures $R_1$ and $R_2$ and the principal directions of curvature can be calculated from a knowledge of the thickness and radius of the wafer 12, the radius of the hollow cylinder 14, the total force F applied to the wafer by the cylinder, and the elastic constants of the material of the wafer 12. In this calculation of the curvature of the wafer 12, it may, in some cases, be sufficient to assume that the wafer is an elastically isotropic material. However, if necessary, it is possible to calculate the curvature with allowance being made for elastic anisotropy. In determining the radii of curvatures $R_1$ and $R_2$, the boundary conditions that apply at the perimeter 16 where the wafer 12 is supported, and where the cylinder 14 makes contact with the wafer 12 are also considered. For example, consideration is made of whether or not the wafer 12 is free to move laterally across the end of the surface 20 of the cylinder 14.

From the curvature of the wafer 12 it is straightforward to calculate the lateral strain in the film 10. For example, consider a case where before deformation the wafer lies in the xy-plane so that the normal to the wafer is the z-direction (see FIG. 4). The x and y directions are selected to lie parallel to the principal directions of the curvature of the wafer 12 at the point of the wafer that will be examined. The stretching of the film 10 in directions lying in the xy-plane, i.e. the lateral strain referred to hereafter as $\eta_{lat}$, is then specified by the elements $\eta_{11}$ and $\eta_{22}$ of the strain tensor. These elements are given by:

$$\eta_{11} = \frac{d}{2R_1} \quad (3)$$

$$\eta_{22} = \frac{d}{2R_2}$$

Thus, from the calculated radii $R_1$ and $R_2$ and the known wafer thickness d it is possible to find the lateral strain in the wafer 12.

There will also be a strain $\eta_{33}$ in the direction normal to the film surface 22. This strain $\eta_{33}$ can be calculated from the condition that the normal stress on the free surface 22 of the film is zero. The result is that $$\eta_{33} = -\frac{2\nu}{1-\nu}(\eta_{11} + \eta_{22}) \quad (4)$$

Because of the strain there will be a stress in the film 10. If the film 10 responds elastically and the strain is sufficiently small the stress can be calculated from the known strain through the use of the equations of linear elasticity. Each element of the stress tensor can be written as a sum of terms; each term equals an element of the strain tensor multiplied by a certain linear combination of the second order elastic constants of the film material. If the film 10 responds elastically and the strain is large, it is necessary to allow for non-linear elastic effects. If plastic flow occurs in the film 10 then the stress will depend on time.

Because of this strain in the film 10 there will be a change $\delta v$ in the sound velocity in the film 10 and also a change $\delta d$ in the film thickness d. These changes will depend on the magnitude and sign of the lateral strain that has been applied by curving the wafer 12. The change in the sound velocity v may be positive or negative and depends on the material composition of the film 10, on the strain, and on the microstructure of the film 10. The change $\delta \tau$ in the acoustic transit time τ through the film is given by:

$$\frac{\delta \tau}{\tau} = \frac{\delta d}{d} - \frac{\delta v}{v} \quad (5)$$

Measurements are now made of the changes $\delta \tau$ in the transit time that result from the application of the force F to the back of the wafer 12. Because the lateral strain in the film 10 is readily related to the applied force F as described above one can consider that such measurements amount to an investigation of the change in the transit time $\delta \tau$ with change in the lateral strain $\eta_{11} = \eta_{22}$.

Figure 6A:
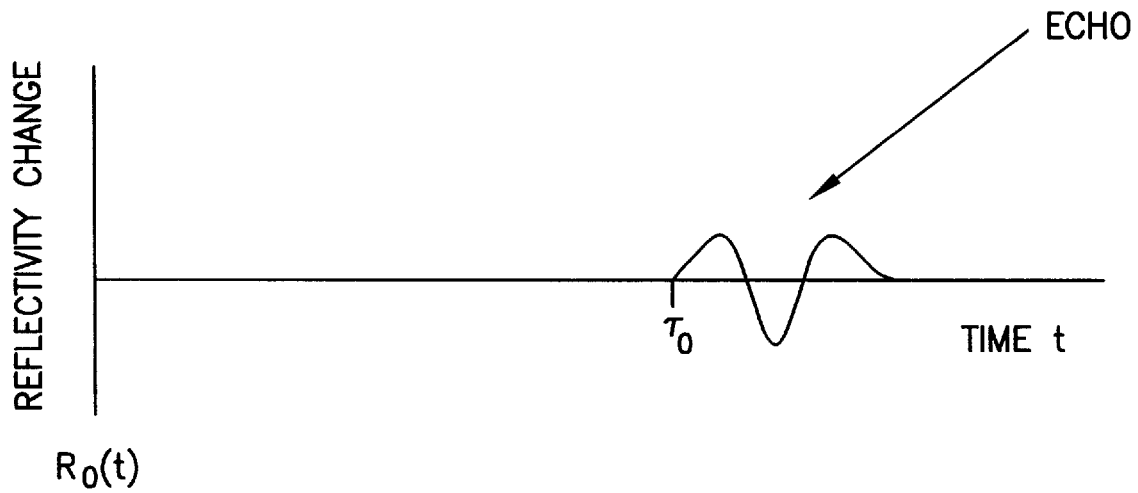
FIGS. 6A–6B are graphs relating the change in optical reflectivity $\Delta R(t)$ with respect to time t for the sample in two different conditions of strain.
Figure 6B:
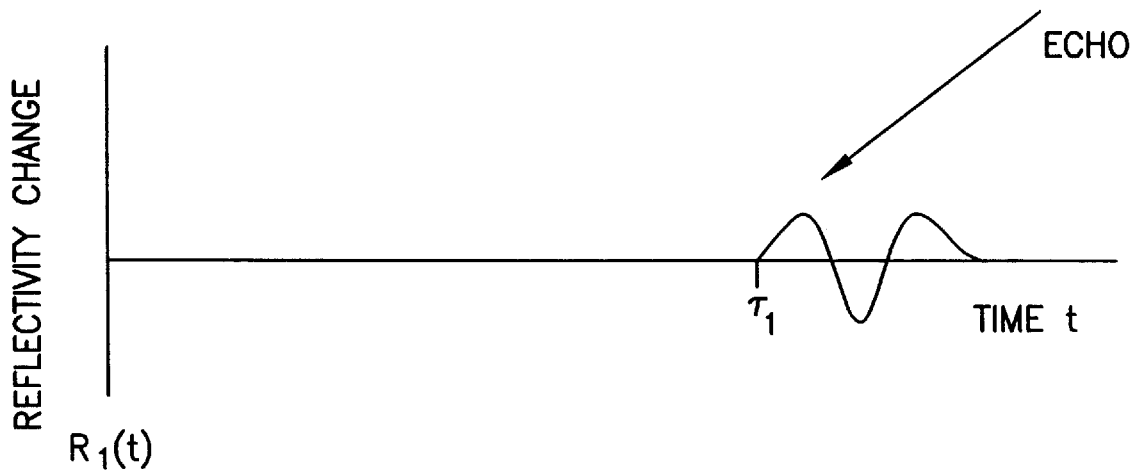
Figure 10:
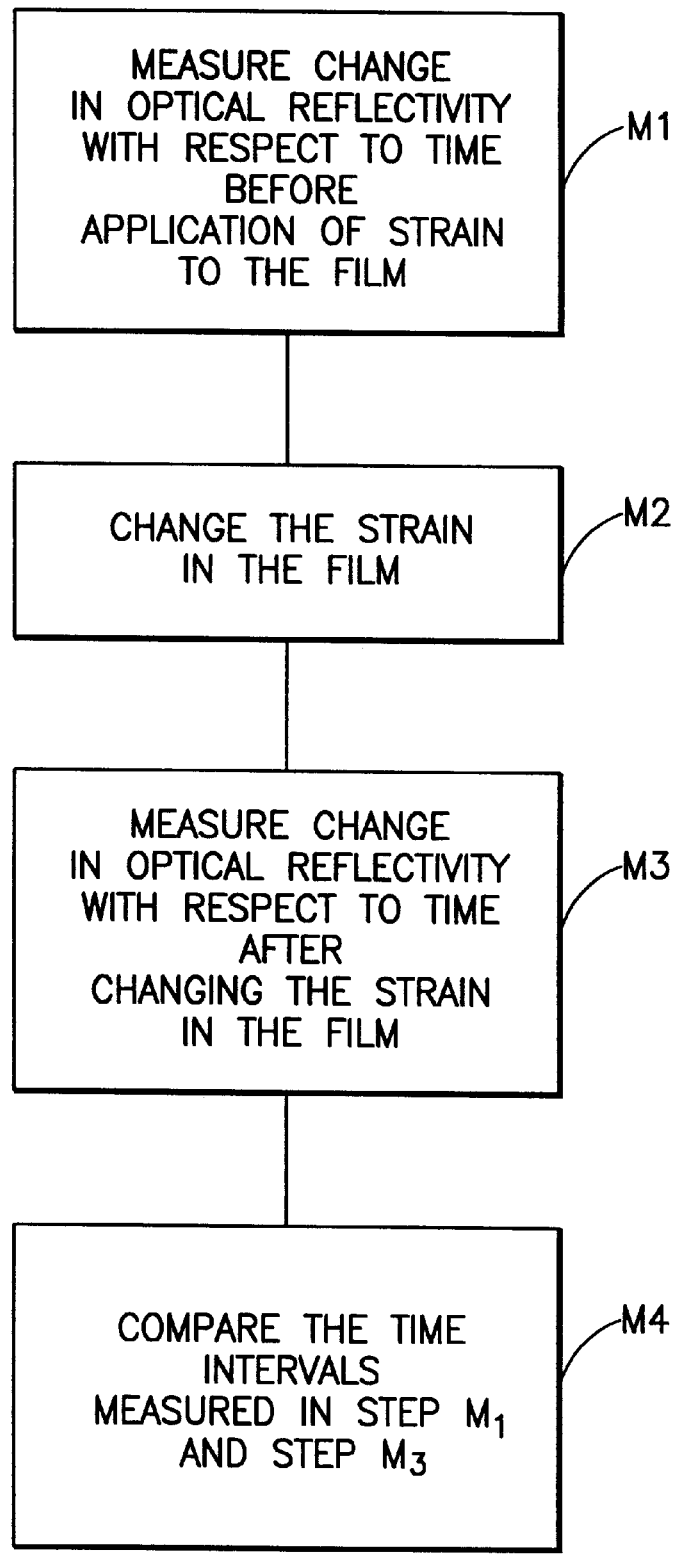
FIG. 10 is a flow chart depicting a first procedure for measuring changes in the time interval $\tau$ for the transit time of a strain pulse in the sample.

The invention makes possible the measurement of extremely small changes $\delta \tau$ in the transit time. Referring now to FIG. 10, there is shown a flow chart diagrammatically depicting the procedure for measuring the change $\delta \tau$ in the transit time of stress pulses in the film 10. In the first step M1, the change in optical reflectivity $\Delta R_0(t)$ as a function of the time interval t is measured with no force applied to the wafer 12. Hence, the initial strain of the film 10 has a value of substantially 0. The change in optical reflectivity $\Delta R_0(t)$ as a function of time is measured using the apparatus 100, 102, 104, 106 and 108 as previously described. The time interval $\tau_0$ for the transit time of the stress pulse in the film 10 is found by measuring the time when the echo feature (see FIG. 6A) is detected in the reflected probe beam. FIG. 6A graphically depicts the change of optical reflectivity $\Delta R_0(t)$ of the probe beam relative to time t before application of strain to the film 10. In FIG. 6A, the time t, since the application of the pump beam to the film 10, is plotted along the abscissa. The change in optical reflectivity $\Delta R_0(t)$ is plotted along the ordinate axis. FIG. 6A shows that, when the strain in the film 10 has a value of substantially 0, the echo feature (i.e. change $\Delta R_0$) in reflectivity of the probe beam is detected at time To. The time $\tau_0$ is recorded in the processor 101 of the apparatus 100, 102, 104, 106 and 108. In the second step M2, a force is applied to the wafer 12 as shown in FIG. 4 to induce a curvature. This results in a change in the lateral strain in the sample film 10 from the initial value to a new value different than the initial value of the strain. The new value of the lateral strain is entered into the processor 101 either as a direct input by the user or as the result of the calculation performed by the processor 101 from the parameters of the wafer 12 and cylinder 14 and the force applied to the wafer 12. The parameters of the wafer 12 and cylinder 14 are entered into the processor 101 by the user. A signal identifying the force applied by the cylinder 14 to the wafer 12 is transmitted to the processor 101 by an appropriate electronic circuit (not shown). Subsequently, in step M3, the change in optical reflectivity $\Delta R_1(t)$ as a function of time t is then measured again. The change in optical reflectivity $\Delta R_1(t)$ is again measured in the same manner as stated above using the apparatus 100, 102, 104, 106 and 108 of this invention. The new time interval $\tau_1$ for the transit time of the stress pulse is found by measuring the time between application of the pulse beam and detection of the echo feature in the reflected probe beam. The new time interval $\tau_1$ for the transit time of the stress pulse in the strained film 10 is shown in FIG. 6B. Similar to FIG. 6A, FIG. 6B graphically depicts the transient change in optical reflectivity $\Delta R_1(t)$ of the probe beam reflected from the strained film 10. FIG. 6B shows that the change or echo feature in the optical reflectivity $\Delta R_1(t)$ arising from the stress pulse in the strained film 10 occurs at time $\tau_1$. The time interval $\tau_1$ is also recorded in the processor 101. Finally in step M4, the time intervals $\tau_0$ and $\tau_1$ corresponding to the changes in optical reflectivity $\Delta R_0(t)$ and $\Delta R_1(t)$ are then compared and the shift in time $\delta\tau$ of the echo feature arising from the returning stress pulse is determined by the processor 101 (see FIGS. 6A–6B). The shift in time $\delta\tau$ is recorded in the processor 101. This shift in time $\delta\tau$ is also the change in transit time of a stress pulse in the film due to the change in strain of the film 10. The above process may then be repeated as required for different values of strain in the film 10, so that the change $\delta\tau$ in transit time may be determined for a range of values of the strain in the film 10. Alternatively, in the transient diffraction grating mode, the initial transit time $\tau_0$ measured in step M1 and the subsequent transit time $\tau_1$ measured in step M3 are measured by detecting the diffracted probe beam (see FIG. 1F). Ultimately, the shift in time $\delta\tau$ is related by the processor 101 to the strain in the film 10 to characterize the film as described in further detail below.

The measurements of the change $\delta\tau$ in transit time may be used in several applications to characterize thin films. One example is the measurement of a certain combination of second and third-order elastic constants of the film and relation to dislocation content of the film. In this application, a lateral strain is applied, in step M3 of the process described above, which is insufficient to cause appreciable plastic flow. The change $\delta\tau$ in the transit time can be calculated from elastic theory and is given by the expression:

$$\frac{\delta\tau}{\tau} = -\left[c_{112} - \frac{\nu}{1-\nu}(c_{111} + 2c_{11})\right]\frac{(\eta_{11} + \eta_{22})}{2c_{11}} \quad (6)$$

where $c_{111}$ and $c_{112}$ are third order elastic constants, and $c_{11}$ is a second order elastic constant. In the derivation of equation 6 it has been assumed that the film material is elastically isotropic. A more general expression that applies to elastically anisotropic materials can also be derived. From the measured value of $\delta\tau/\tau$ (i.e. measured in accordance with the process described above) for a known applied strain, and using an assumed or measured value of $C_{11}$, the quantity C defined by the equation:

$$C = c_{112} - \frac{\nu}{1-\nu}(c_{111} + 2c_{11}) \quad (7)$$

can be determined. It is well known that for materials containing dislocations the effective values of the third order elastic constants are significantly affected by the dislocation density. Hence, a measurement of the value of C and comparison with the value calculated from Eq. 7 using values of $c_{112}$, $c_{111}$, $c_{11}$, and $\nu$ measured on bulk materials with known dislocation densities can be used to make an estimate of the dislocation density in the film.

Another application of the above described method is for determination of the yield stress of the film 10. As is indicated in Eq. 7 when the strain in the film is small and the film material responds elastically, the change in the sound velocity is proportional to the strain. In this range of strain the film is behaving elastically. When the lateral strain is sufficiently large the stress in the material will exceed the yield stress, and plastic flow will occur. Above this critical value of the lateral strain, the change $\delta\tau$ in the transit time will no longer increase linearly with lateral strain $\eta_{lat}$. Hence, by determination of the value of $\eta_{lat}$ at which $\delta\tau$ ceases to increase linearly with $\eta_{lat}$, the lateral strain $\eta_{yield}$ at which plastic flow begins can be determined. Therefore, in this application, the process depicted in FIG. 10 is repeated for a range of strains n sufficient to include $\eta_{yield}$. The value of $\eta_{yield}$ is found by comparing the measured time intervals $\tau$ corresponding to different values of strain $\eta$ to locate the strain $\eta$ where the measured changes $\delta\tau$ in transit time are no longer linearly related to the changes in the strain $\eta$ in the film 10. From $\eta_{yield}$ the yield stress $\sigma_{yield}$ can be determined through the use of the equation:

$$\sigma_{yield} = \frac{(1+\nu)(1-2\nu)}{(1-\nu)^2}c_{11}\eta_{yield} \quad (8)$$

Still another application of the above method is determination of the rate of plastic flow of the material in the film 10. As already mentioned above, for some materials, the application of a stress results in a strain which increases steadily with time at a significant rate. For such materials if the lateral strain is held constant, the stress will decrease as time increases. Also, after a long time the material will tend to relax towards a state in which the volume has returned to its original value. During this relaxation the magnitude of the strain $\eta_{33}$ in the direction perpendicular to the plane of the film 10 will increase. The rate at which this relaxation occurs can be determined by measurement of the changes $\delta\tau$ in the transit time that take place when the sample is maintained in a state with constant $\eta_{lat}$. Thus, for example, the transit time can be measured at a series of equally-spaced times while the lateral strain was held constant.

Yet still another application of the previously described method is determination of mechanical properties based on measurement of echo amplitudes of the reflected probe beam. The presence of dislocations in the film results in an attenuation of the propagating stress pulse as it passes through the film. Hence when plastic flow occurs and the number of dislocations in the film increases, the amplitude that the stress pulse will have after propagation through the sample will be decreased. This decrease will reduce the magnitude of the echo feature in $\Delta R(t)$ that arises from the stress pulse arriving at the surface of the film. The applied lateral strain may also result in a modification of the quality of the mechanical bonding at the interface between the film and the substrate. This change in bonding will also result in a change in the amplitude of the returning stress pulse, and a change in the size of the echo feature in $\Delta R(t)$ that arises from the stress pulse arriving at the surface of the film. In this application, the process depicted in FIG. 10 is modified by adding an additional step (not shown) wherein the change in amplitude of the reflected probe beam is measured relative to the strain induced in the film 10.

It is also within the scope of this invention to use other methods for inducing a curvature in the substrate. For example, a number of forces of chosen magnitude can be applied at selected locations on the wafer to induce the desired curvature. It is also possible to apply forces distributed over chosen lines or areas of the wafer. It is also possible to apply lateral forces to the wafer, for example, at the perimeter of the wafer. Then the wafer would not be curved but instead would be stretched in the plane of the wafer.

It is also within the scope of this invention to apply a lateral strain to the sample film by means other than bending the wafer substrate. For example, the wafer and film can be heated from a starting temperature $T_0$ to a new temperature $T_1$. If the coefficients of linear thermal expansion of the substrate and the film are a $\alpha_{substrate}$ and $\alpha_{film}$ respectively, then the lateral strain in the film that results from the temperature change from $T_0$ to $T_1$ is $$\eta_{lat} = (\alpha_{substrate} - \alpha_{film})(T_1 - T_0) \qquad (9)$$

Here strain is defined as the distortion of the film relative to the configuration the film would have in a stress-free state at the temperature $T_1$. In this alternative method the value of the lateral strain $\eta_{lat}$ can be controlled by changing the temperature $T_1$. Compared to the method in which the wafer 12 is curved by application of forces (see FIG. 4), this alternative method has the advantage that there is no danger that the wafer will break. However, this alternative method has the relative disadvantage that the temperature of the film is changed while the measurement is being made. Hence, for a more complete characterization of the properties of the film it may be advantageous to perform a comprehensive investigation in which the temperature is varied and, in addition, forces are applied, as shown in FIG. 4, so as to vary the curvature of the wafer, or to stretch the wafer. Such measurements could be used, for example, to determine the yield stress as a function of temperature.

Corresponding to the strain induced in the film by the differential thermal expansion of the film relative to the substrate, a state of stress $\sigma$ is also induced in the film. The magnitude of this stress will be proportional to the temperature change $\delta T$ from the starting temperature $T_0$ to the new temperature $T_1$. The change in the acoustic transit time $\delta\tau$ of the film due to the change in temperature $\delta T$ has contributions from the change in the film thickness of the thin film, the change in sound velocity due to the change in temperature as well as the change in the sound velocity due to the change in stress or lateral strain $\eta_{lat}$. For a small change in temperature $\delta T$ each of these contributions will be proportional to the change in temperature $\delta T$. However, after the temperature has been raised by a critical amount $\delta T_c$ the stress induced in the film by the dissimilar rates of thermal growth becomes sufficient to induce plastic flow in the film. The linear relation between the change in transit time $\delta\tau$ and the change in temperature $\delta T$ no longer holds after plastic flow occurs in the film. Hence, the stress at which plastic flow begins can be found by detecting the point where the change in acoustic transit time $\delta\tau$ as detected by the apparatus 100, 102, 104, 106 and 108 are no longer linear with changes in temperature $\delta T$ of the film.

The temperature can be changed by placing the wafer substrate and film within an oven and varying the temperature of the oven with time by means of a computer-controlled temperature controller, for example. Alternatively, a small region of the film and underlying substrate can be heated by means of optical radiation focussed onto the film (see FIG. 1A) or onto the back of the substrate. With this second technique, several methods are available to determine the temperature of the film and the temperature of the substrate. For example, the power of the optical radiation source, the area of illumination, and the fraction of radiation which is absorbed at the surface can be measured. The power absorbed per unit area is then calculated. From a further knowledge of the thermal conductivity of the substrate, the substrate thickness and the emissivity of the film and substrate for thermal radiation, it is then possible to calculate the temperature rise and distribution in the film and substrate. The temperature change in the film can also be measured by optical pyrometry.

It is also within the scope of this invention to raise the temperature of the sample for a very short period of time so that the lateral strain is present in the film for only this period. This variation of the measurement is best accomplished through the use of heating by an optical radiation source (see FIG. 1A) which can deposit a known amount of heat into the sample within a short and known time interval. The time of application of the heat could be made as short as 1 picosecond by using a pulsed laser as a heat source.

It is also within the scope of the invention to apply a stress to the sample by other means, and to use this stress to induce a plastic flow of the film material. For example, the following procedure can be used. First, the round trip time $\tau_a$ for stress pulses in the film is measured by the method already described. Second, a large amplitude stress pulse is then generated in the film by application of a short laser pulse of high energy. If the transient stress in the film exceeds the yield stress of the film material it will induce a plastic flow. Third, the round trip time $\tau_c$ for stress pulses in the film is again measured and compared with the result $\tau_a$ obtained first. If plastic flow has occurred there will be a difference between the transit time $\tau_a$ and $\tau_c$. The stress pulse generated in the sample to induce plastic flow, in the second step, is much larger than the stress pulses used for measuring the transit times in the first and third steps. The stress pulse in the second step can be generated directly in the film, or alternatively, can be generated by absorption of a laser pulse at the back of the substrate wafer.

Figure 11:
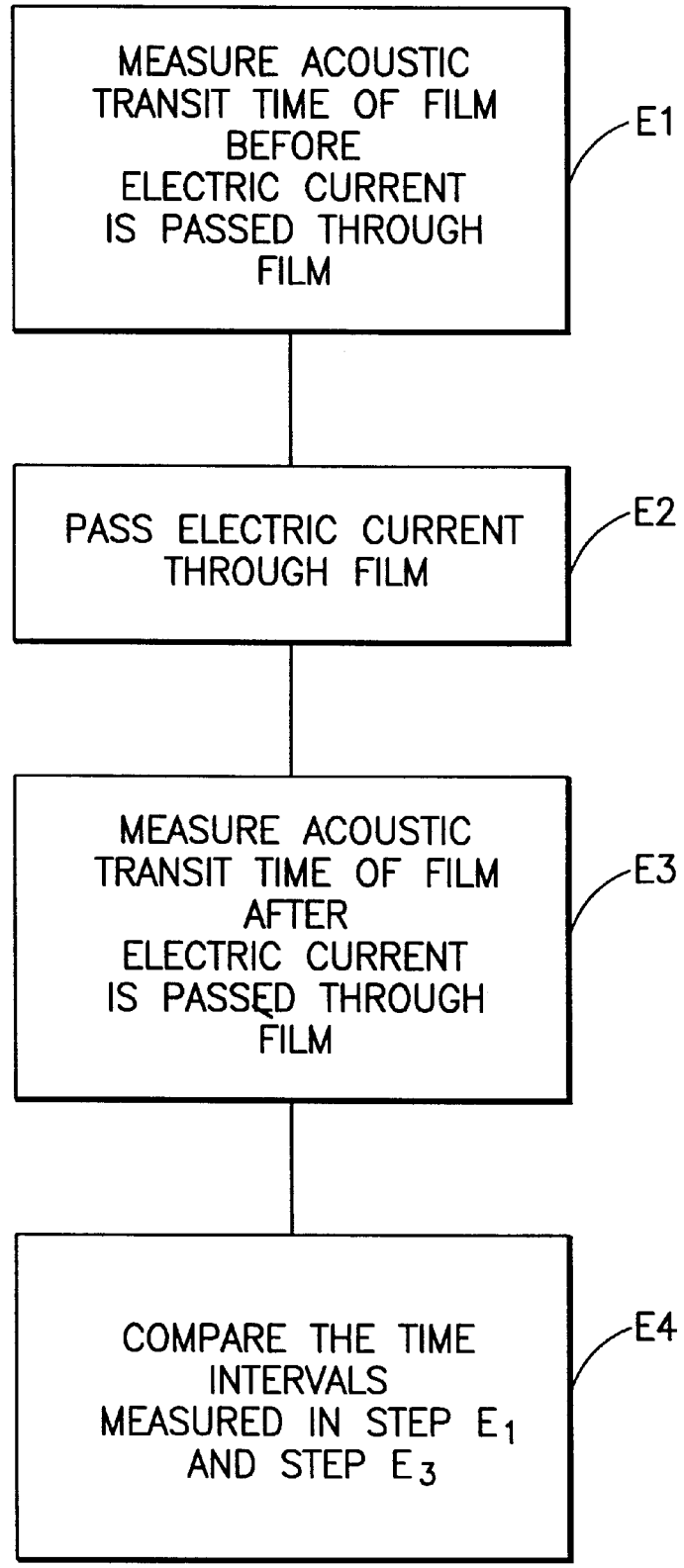
FIG. 11 is a second flow chart depicting a second procedure for measuring changes in the time interval $\tau$ for the transit time of a strain pulse in the sample.

In yet still another application of the present invention, the rate of electromigration in a metal film is measured. The process for measuring the rate of electromigration in the film is graphically depicted in the flow chart shown in FIG. 11. In the first step E1, the acoustic transit time (i.e. the round trip time of a stress pulse in the thin film) through the metal film is measured by measuring the initial transient optical response of the film as previously described for step M1 of the process shown in the flow chart of FIG. 10. Next, in step E2, an electric current is passed through the film (in the direction parallel to the substrate). After the electric current is passed through the film, the acoustic transit time through the film is again measured in step E3, again by measuring the new transient optical response of the film. Then in step E4, the transit times measured in steps E1 and E3 are compared to determine the change $\delta\tau$ in acoustic transit time due to passing an electric current through the film. These changes $\delta\tau$ in transit time arise because the thickness of the film is changed as a result of the electromigration. It is also possible for the sound velocity to be affected by electromigration if the concentration of vacancies in the metal film is modified. This change in sound velocity, if it occurs, also contributes to the change in the transit time. To measure electromigration, it is not necessary to apply forces to curve or stretch the wafer. Thus, the sample stage 122 of the apparatus 100, 102, 104, 106 and 108 need not have the force applying cylinder 14, but is otherwise modified to allow passing an electric current through the sample. The shift in transit time $\delta\tau$ is calculated by the processor 101 from the detected transients in optical response of the sample and is related by the processor 101 to the rate of electromigration of the sample. Before using the apparatus 100, 102, 104, 106 and 108 to measure the rate of electromigration of the sample, it is desirable to calibrate the apparatus using a test sample having a know rate of electromigration.

To make measurements of electromigration a number of different variations of the above method can be used. A flow of current in the film results in a flux of atoms. The rate of change of the thickness of the film with time depends on the variation of this atomic flux with position. Variations in the atomic flux can result from a variation in the current density with position and/or a variation in the temperature of the film with position. The atomic flux increases with increase in both current density and temperature. Two methods for measuring the rate of electromigration will now be described with reference to FIGS. 7 and 8.

Figure 7:
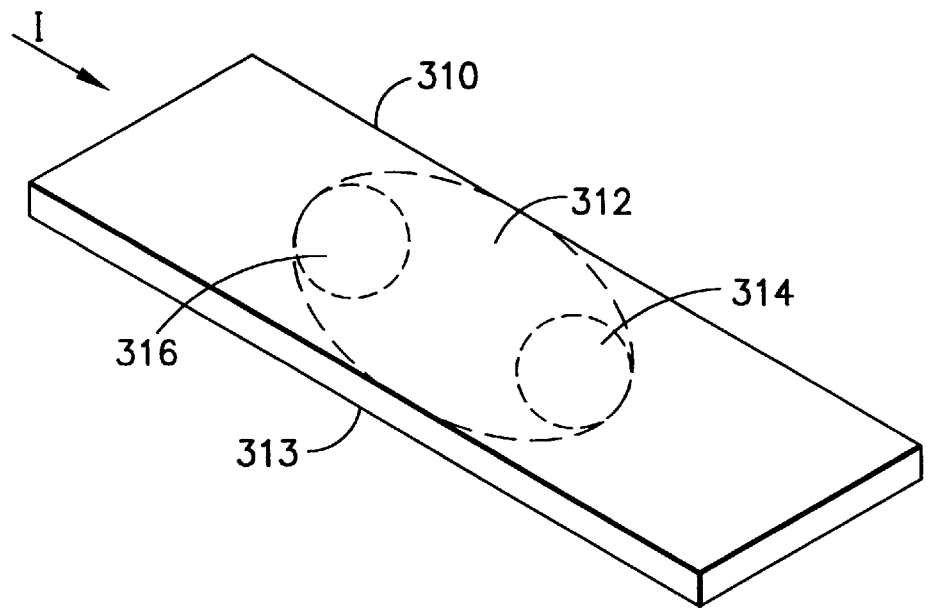
FIG. 7 is a schematic perspective view of a sample to be characterized in accordance with a second method of this invention, the sample having an electrical current passed therethrough.

Referring now to FIG. 7, there is shown a perspective view of a film 310 in the form of a strip of uniform width and thickness. A current I is passed along the film 310. The temperature in a section 312 of the film 310 is raised relative to the remainder of the film. The temperature increase may be achieved through the use of optical illumination of the film 310, by heating of the region 313 of the substrate underneath the section 312 of the film 310,or by other means. At the ends 314, 316 of the section 312 of the film 310 within which the temperature has been increased there will be a temperature gradient. Because of this temperature gradient, the atomic flux due to electromigration will vary along the film 310. This will cause an increase in the thickness of the film 310 at one end 314, 316 and a decrease at the other. By making measurements of the acoustic transit time at the locations of either or both of these ends 314, 316 of section 312, the rate of electromigration in the film 310 can be determined.

Figure 8:
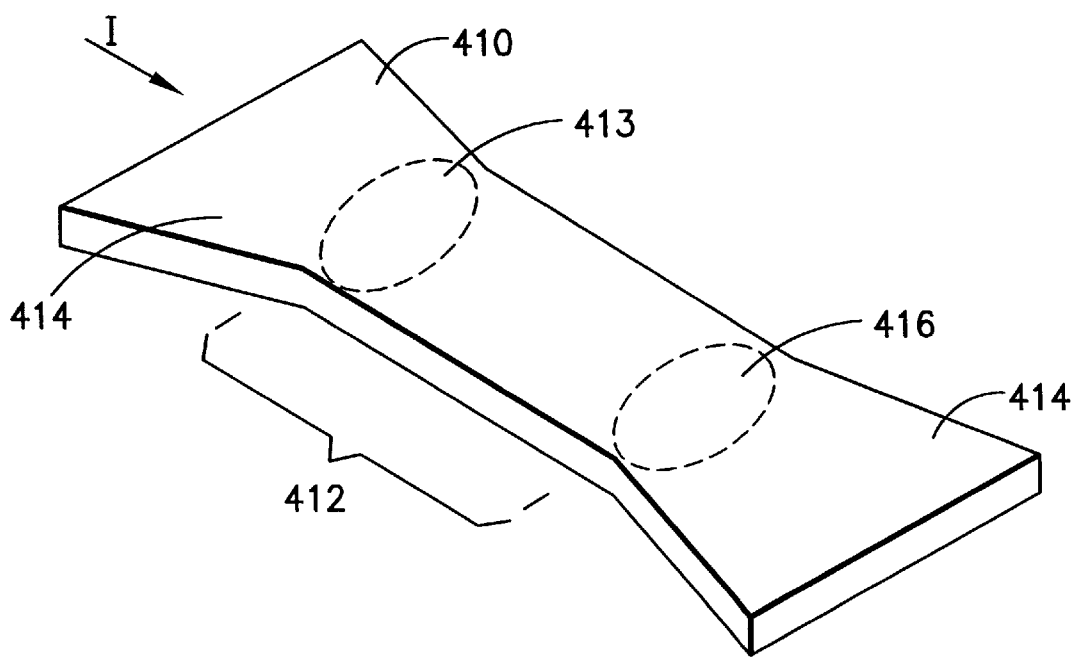
FIG. 8 is a schematic perspective view of a sample to be characterized in accordance a first variation of the second method of this invention, the sample having a section of reduced width.

Referring now to FIG. 8 there is shown a schematic perspective view of a film 410 which has a width,or the thickness, that changes along the length of the film 410. The film 410 has a section 412 with a reduced width. If a current is passed along the film 410, the current density in the section 412 of the film with reduced width will be greater than in the remaining section 414 of the film. As a consequence, there will be a gradient in the atomic flux in the regions 416 and 418 at the ends of the section 412 of reduced width. Hence, in these regions 416, 418 the thickness of the film will change with time and a measurement of this rate of change will determine the rate of electromigration in the film 410.

It is also within the scope of the invention to find the rate of electromigration in thin films by measuring the Soret flux. Electromigration is the motion of atoms or vacancies that result from the passage of an electric current through a material. In the absence of an electric current, atoms or vacancies diffuse randomly through a material. The electric current, and the electric field which drives the current, produce a force F on each atom or vacancy. Under the influence of this force, the diffusion of atoms and vacancies ceases to be completely random and so there is a net flux of atoms in a direction determined by the direction of the current. The magnitude $J_{atom}$ of this flux of atoms or vacancies is determined by the force F and the diffusion coefficient D (see Huntington and Grone). The magnitude of both the force F and the diffusion coefficient D depend on the microstructure of the film material. The diffusion coefficient D determines the flux of atoms or vacancies that results from a gradient in the concentration of atoms or vacancies. A flux of atoms or vacancies can also result from a temperature gradient (i.e. the Soret effect), even in the absence of a concentration gradient. The magnitude of this flux is again determined by the ease with which atoms or vacancies can move through the material. Thus, in some circumstances, it is sufficient to measure the flux due to the temperature gradient (i.e. the Soret flux) and based on the result of this measurement to make an estimate of the rate at which electromigration will occur in the presence of an electric current. This approach has the advantage that the Soret flux is measured without having to pass a current through the film sample. The method for measuring the Soret flux is similar to that described previously with reference to FIG. 11, except that no electric current is applied to the film sample to measure the Soret flux. Thus, the method to measure the Soret flux comprises the steps of measuring an initial acoustic transit time in the film sample by detecting the change in optical reflectivity $\Delta R(t)$ of the film. Then a region of the film sample is heated to create a temperature gradient. Preferably, the heated region of the film is generated by using a pulsed or a continuous light source. However, any other suitable means may be used to heat the region of the film. After the film is heated, the acoustic transit time in the film is measured again in a portion of the heated region with a sufficient temperature gradient. Finally, the pre-heat and post-heat transit times are compared and the difference between the transit times is related to the change in thickness of the film sample due to the Soret flux.

The present invention may also be used to measure electromigration in a thin film by observing the change in optical reflectivity $\Delta R(t)$ of the probe beam due to changes in the surface topology of the metal film. When electromigration takes place, there is often a change in the surface topology of a metal film in addition to the change in thickness of the film. The surface of the film may become irregular and hillocks may appear. This change in the film surface will result in a change in the way the strain pulse is reflected at the film surface and will reduce the amplitude of the change of the reflected probe beam $\Delta R(t)$ (i.e. the amplitude of the echo in $\Delta R(t)$, see FIGS. 6A, 6B). In this application, the method for determining the rate of electromigration in a film depicted in FIG. 11 and described above is modified by adding an additional step (not shown) wherein the change in amplitude of the reflected probe beam due to the returning strain pulse (i.e. the strength of the echo in $\Delta R(t)$) is compared over time.

The invention has been described above as it applies to the measurement of mechanical properties and rate of electromigration of a single thin film which has been deposited onto a substrate. The invention can also be applied to the measurement of the mechanical properties and rate of electromigration of more complex structures consisting of a number of thin films deposited as a sequence on top of a substrate (often referred to as a stack). Some of the films may be transparent and some optically absorbing. As a consequence, the light of the pump pulse will be strongly absorbed in some of the films and weakly absorbed or not absorbed at all in other of the films. Strain pulses will be generated within each of the films in which light is absorbed. The strain pulses will propagate through the structure and will be partly reflected and partly transmitted at each interface that is encountered. There will be a change $\Delta R(t)$ in the optical reflectivity that will contain features from which the acoustic transit times through the different films making up the structure can be determined. To make this determination it is desirable to perform a computer simulation the results of which are compared with the measured change in optical reflectivity $\Delta R(t)$. In the computer simulation, the propagation of strain pulses through the structure is calculated taking account of the various acoustic reflections that take place at the interfaces between the different film layers. From the calculated strain distribution in the structure, the change $\Delta R(t)$ in optical reflectivity corresponding to the transit time of a strain pulse through the particular film layers in the sample is then calculated. In this calculation, it is an advantage if the index of refraction of some, or all of the films has been previously determined through ellipsometric measurements. The ellipsometer mode of apparatus 102 described previously (see FIG. 1B) is used to measure the index of refraction of the particular films. The parameters of the structure (e.g. the thickness of the different films) are then adjusted so as to give a best fit between the calculated and measured change in optical reflectivity $\Delta R(t)$. Once the parameters of the structure are determined, then the transit time through a particular film in the sample is found. From the change in the transit time through a particular film the mechanical properties, such as the yield stress and the rate of electromigration, of that film can be studied. For example, the change in thickness of each film can be found, and from this the rate of electromigration in each film can be determined. Also, the changes in the amplitude of the different features in $\Delta R(t)$ can be used to deduce changes in dislocation density in the films and changes in bonding at interfaces. In addition, the invention can be applied to the measurement of the mechanical properties and electromigration of laterally patterned structures.

It is also within the scope of the invention to measure other transient optical properties instead of the change in the optical reflectivity. As previously mentioned, the apparatus 100, 102, 104, 106 and 108, as shown in FIGS. 1A–1E, are capable of measuring the (1) transient change in the reflectivity $\Delta R(t)$ of the probe beam. With suitable modifications the apparatus can be used to measure (2) the change $\Delta T$ in the intensity of the transmitted probe beam, (3) the change $\Delta P$ in the polarization of the reflected probe beam, (4) the change $\Delta\phi$ in the optical phase of the reflected probe beam, and/or (5) the change in the angle of reflection $\Delta\beta$ of the probe beam. These quantities may all be considered as transient responses of the sample which are induced by the pump pulse. These measurements can be made together with one or several of the following: (a) measurements of any or all of the quantities (1)–(5) just listed as a function of the incident angle of the pump or probe light, (b) measurements of any of the quantities (1)–(5) as a function of more than one wavelength for the pump and/or probe light, (c) measurements of the optical reflectivity through measurements of the incident and reflected average intensity of the pump and/or probe beams; (d) measurements of the average phase change of the pump and/or probe beams upon reflection; and/or (e) measurements of the average polarization and optical phase of the incident and reflected pump and/or probe beams. The quantities (c), (d) and (e) may be considered to be average or static responses of the sample to the pump beam.

Figure 5:
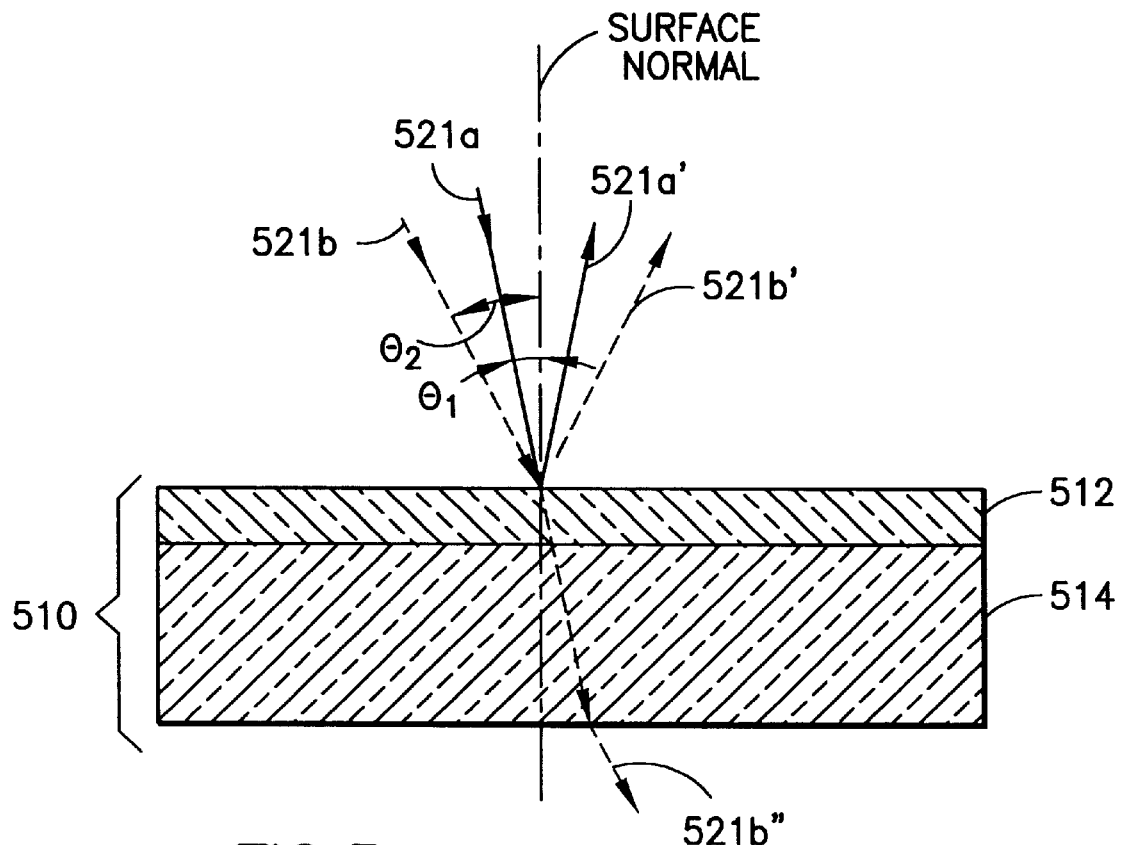
FIG. 5 is a schematic cross-sectional view of an optically transparent sample comprising an optically transparent thin film and an optically transparent substrate.

It is also within the scope of the invention to use an alternative measurement method which has special advantages for measuring the response of optically transparent films to applied stress. Referring now to FIG. 5, there is shown a sample 510 comprising a thin film 512 deposited on a substrate 514. Both the thin film 512 and the substrate 514 are optically transparent to the extent that the sample 510 has the property that the incident light penetrates at least one wavelength into a layer (i.e. the thin film 512) or layers (i.e. the thin film 512 and the substrate 514) into which a stress wave is launched. The apparatus of this invention 100, 102, 104, 106 and 108 is used to apply a pulse beam 521a and a probe beam 521b to the sample 510 in a manner as described previously. For this sample 510, it is possible to use picosecond ultrasonics to independently measure the sound velocity and refractive index of said thin film layer 512 or thin film and substrate layers 512, 514 with great precision.

The sound velocity may also be used to determine the elastic modulus. Optical interference between probe light reflected from the surface of the sample and probe light reflected from the traveling stress wave gives rise to oscillations in the intensity of the reflected probe beam 521b' as a function of delay of time between the application of the pump beam 521a and that of the probe beam 521b to the sample 510. The period of these oscillations may be measured very precisely. For a material having an index of refraction n and sound velocity $v_s$ the period of the oscillations is given by:

$$\tau = \frac{\lambda_0}{2nv_s\cos\theta} \qquad (10)$$

where $\lambda_0$ is the optical wavelength in free space and $\theta$ is the angle between the direction normal to the surface of the sample 510 and the direction of probe light propagation in the sample. Typically one knows $\theta$ and $\lambda_0$ in advance. Thus, from the observed oscillation period, one can deduce the product $nv_s$ with high precision. The value of $v_s$ independent of n can be found by measuring $\tau$ at a second angle $\theta$ (which yields a value for n), or by using a published value for n. The angle $\theta$ is changed by tilting the sample stage 122 of the apparatus 100, 102, 104, 106 and 108. From the sound velocity, the elastic modulus $c_{11}=\rho v_s^2$ of the transparent film may be determined directly (using a previously determined value of $\rho$). This method also makes it possible to determine small changes $\delta v$ and $\delta n$ in the sound velocity $v_s$ and the refractive index n, rather than simply the change $\delta\tau$ in the round trip time $\tau$. The changes $\delta n$ in the refractive index and $\delta v$ in the sound velocity are then related to the applied stress in the film in a manner substantially similar to that described previously with reference to FIG. 10 for relating the changes in transit time $\delta\tau$ to applied stress.

It is also within the scope of the invention to make measurements on films which are so thin that the spatial extent of the generated strain pulse (in the direction normal to the plane of the film) is comparable to the thickness of the film. For such films it is not useful to consider that the generated strain pulse bounces back and forth within the sample. Instead, one should consider that the pump pulse excites the film into its fundamental vibrational thickness mode. Under these conditions the change in optical reflectivity $\delta R(t)$ will vary periodically with the time t. The period of this vibration is the period of the fundamental vibrational thickness mode. Measurement of this period as a function of applied lateral strain can be used to determine the mechanical properties of the sample, such as the yield stress. Measurement of the period can be also used to determine the rate of electromigration.

It is also within the scope of the invention to measure a change in the Kapitza conductance when plastic flow occurs. The Kapitza conductance can be measured by an analysis of the background part of the change in the optical reflectivity (or other transient optical response). The background part of the change in optical reflectivity is the part of the response that varies smoothly with time (i.e. the part that comes from the change in temperature of the metal film rather than due to propagating strain pulses). Thus, from an analysis of the background part we can determine the Kapitza conductance $\sigma_K$, and from measuring how UK changes when the metal film is strained we can determine the yield stress of the metal film.

Therefore, while the invention has been particularly shown and described with respect to preferred embodiments thereof, it will be understood by those skilled in the art that changes in form and details may be made therein without departing from the invention. Accordingly, the present invention is intended to embrace all such alternatives, modifications and variances which fall within the scope of the appended claims.

What is claimed is:

1. A method for characterizing a sample, comprising the steps of:
   measuring a first change in optical response of the sample, the sample having an initial lateral strain when the first change in optical response is measured;
   changing the lateral strain of the sample from the initial lateral strain to a different lateral strain;
   measuring a second change in optical response of the sample, the sample having the different lateral strain when the second change in optical response is measured;
   comparing the second change in optical response relative to the first change in optical response to find a difference between the second change and first change in optical response of the sample; and
   associating the difference between the second change in optical response and the first change in optical response with a property of interest in the sample.

2. A method as in claim 1, wherein the step of measuring the first change in optical response comprises measuring the first change in optical response of the sample as a function of time, and wherein the step of measuring the second change in optical response comprises measuring the second change in optical response of the sample as a function of time.

3. A method as in claim 2, wherein the step of comparing comprises comparing the second change in optical response as a function of time relative to the first change in optical response as a function of time to find a time difference between the second change and first change, and wherein the step of associating comprises associating the time difference with a property of interest in the sample.

4. A method as in claim 1 wherein the sample is a thin film of between 100 Å and 10μ.

5. A method as in claim 1 wherein the step of changing the lateral strain of the sample comprises the steps of clamping a substrate at an outer perimeter of the substrate and deflecting a portion of the substrate interior to the outer perimeter of the substrate, the substrate having the sample disposed thereon.

6. A method as in claim 5 wherein the step of deflecting a portion of the substrate comprises applying a force to the interior portion of the substrate, the force being aligned generally perpendicular to the substrate.

7. A method as in claim 1 wherein the step of measuring the first change in optical response comprises the steps of:
   applying a first pulse of light to a surface of the sample for creating a propagating strain pulse in the sample;
   applying a second pulse of light to the surface of the sample so that the second pulse of light interacts with the propagating strain pulse in the sample; and
   sensing from a reflection of the second pulse of light from the sample the first change in optical response of the sample.

8. A method as in claim 1, wherein the sample is a metal film made of copper or aluminum.

9. A method as in claim 1, wherein the sample includes a stack comprising a plurality of thin films and wherein the step of associating comprises associating the difference between the second change in optical response of the sample and the first change in optical response of the sample with a property of interest of a predetermined film in the stack.

10. A method as in claim 1, wherein the sample comprises an optically transparent thin film.

11. A method as in claim 1, wherein the step of measuring the first change in optical response comprises measuring an amplitude of the first change in optical response, the step of measuring a second change in optical response comprises measuring an amplitude of the second change in optical response, the step of comparing comprises comparing the amplitude of the second change with the amplitude of the first change in optical response to find a difference in amplitude, and wherein the step of associating comprises associating the difference in amplitude to a quantity of dislocations in the sample.

12. A method as in claim 1, wherein the property of interest is a yield stress of the sample.

13. A method as in claim 1, wherein the property of interest is a plastic flow rate of the sample.

14. A method as in claim 1, wherein the property of interest is an elastic constant of the sample.

15. A method as in claim 1, wherein the step of measuring the first change in optical response comprises the steps of:
   applying a plurality of pump light pulses to the sample to result in constructive and destructive interference therebetween and induce a spatially varying strain pulse in the sample;
   applying a probe light pulse to interact with the strain pulse in the sample; and
   sensing from a diffracted probe light pulse the first change in optical response of the sample.

16. A method for measuring a rate of electromigration in a thin metal film, comprising the steps of:
   measuring a first change in an optical response of the metal film;
   passing an electrical current through the metal film;
   measuring a second change in the optical response of the metal film after passing the electrical current through the film;
   comparing the second change in optical response relative to the first change in optical response to find a difference between the second change and first change in optical response of the metal film; and
   relating the difference to the rate of electromigration in the metal film.

17. A method as in claim 16, wherein the step of measuring the first change in optical response comprises measuring the first change in optical response of the thin film as a function of time, and wherein the step of measuring the second change in optical response comprises measuring the second change in optical response of the thin film as a function of time.

18. A method as in claim 17, wherein the step of comparing comprises comparing the second change in optical response as a function of time relative to the first change in optical response as a function of time to find a time difference between the second change and first change, and wherein the step of relating comprises relating the time difference to the rate of electromigration in the thin film.

19. A method as in claim 16 further comprising the step of raising the temperature of one portion of the metal film relative to the remainder of the metal film.

20. A method as in claim 19 wherein the step of raising the temperature of the one portion of the metal film is performed substantially coincident with the step of passing the electric current through the film.

21. A method as in claim 16 wherein the metal film has two end sections with a mid-section therebetween, the mid-section having a reduced width in comparison to the two end sections of the film.

22. A method as in claim 16, wherein the step of measuring the first change in optical response comprises measuring an amplitude of the first change in optical response, the step of measuring a second change in optical response comprises measuring an amplitude of the second change in optical response, the step of comparing comprises comparing the amplitude of the second change with the amplitude of the first change in optical response to find a difference in amplitude, and wherein the step of relating comprises relating the difference in amplitude to a rate of electromigration in the thin film.

23. A non-destructive system for characterizing a thin film, comprising:

a stage holding a substrate of a predetermined thickness thereon, the thin film being located on a first side of the substrate;

means for applying an optical pump pulse and an optical probe pulse to a free surface of the thin film, the probe pulse being temporally delayed from the pump pulse;

means for detecting a change in optical response with respect to time of the probe pulse reflected from the surface of the thin film; and means for changing strain in the thin film from an initial strain value to a different strain value.

24. A non-destructive system as in claim 23 wherein the means for changing strain comprise a mechanical force applicator member contacting a second side of the substrate opposite the thin film to apply a force to the substrate.

25. A non-destructive system as in claim 24 wherein the mechanical force applicator member is substantially perpendicular to the substrate when the mechanical force applicator member contacts the substrate.

26. A non-destructive system as in claim 24 wherein the mechanical force applicator member has a generally cylindrical shape with a diameter of a predetermined size.

27. A method for measuring a rate of electromigration in a sample comprising the steps of:

measuring a first transient optical response of the sample;

heating a portion of the sample to induce a temperature gradient in the sample;

measuring a second transient optical response of the sample in the heated portion of the sample; and relating a difference between the second transient optical response and the first transient optical response of the sample to the rate of electromigration in the sample.

* * * * *